(12) United States Patent
Liu et al.

(10) Patent No.: US 11,753,471 B2
(45) Date of Patent: *Sep. 12, 2023

(54) ANTI-PD-1/ANTI-HER2 NATURAL ANTIBODY STRUCTURAL HETERODIMERIC BISPECIFIC ANTIBODY AND METHOD OF PREPARING SAME

(71) Applicants: BEIJING HANMI PHARMACEUTICAL CO., LTD., Beijing (CN); INNOVENT BIOLOGICS (SUZHOU) CO., LTD., Jiangsu (CN)

(72) Inventors: Jiawang Liu, Beijing (CN); Nanmeng Song, Beijing (CN); Yaping Yang, Beijing (CN); Maeng Sup Kim, Beijing (CN); Yao Yan, Jiangsu (CN); Qingqing Yin, Jiangsu (CN)

(73) Assignees: BEIJING HANMI PHARMACEUTICAL CO., LTD., Beijing (CN); INNOVENT BIOLOGICS (SUZHOU) CO., LTD., Jiangsu (CN)

(*) Notice: Subject to any disclaimer, the term of this patent is extended or adjusted under 35 U.S.C. 154(b) by 122 days.

This patent is subject to a terminal disclaimer.

(21) Appl. No.: 16/968,241

(22) PCT Filed: Feb. 8, 2019

(86) PCT No.: PCT/IB2019/051008
§ 371 (c)(1),
(2) Date: Aug. 7, 2020

(87) PCT Pub. No.: WO2019/155408
PCT Pub. Date: Aug. 15, 2019

(65) Prior Publication Data
US 2021/0032343 A1 Feb. 4, 2021

(30) Foreign Application Priority Data

Feb. 8, 2018 (WO) ............... PCT/CN2018/075851

(51) Int. Cl.
```
C07K 16/00    (2006.01)
C07K 16/28    (2006.01)
A61P 35/00    (2006.01)
C07K 16/32    (2006.01)
A61K 39/00    (2006.01)
```

(52) U.S. Cl.
CPC .......... *C07K 16/2818* (2013.01); *A61P 35/00* (2018.01); *C07K 16/32* (2013.01); *A61K 2039/505* (2013.01); *C07K 2317/31* (2013.01); *C07K 2317/52* (2013.01); *C07K 2317/55* (2013.01); *C07K 2317/622* (2013.01); *C07K 2317/76* (2013.01); *C07K 2317/90* (2013.01)

(58) Field of Classification Search
CPC ............................ C07K 16/2818; C07K 16/32; C07K 2317/31; C07K 2317/52; C07K 2317/55; C07K 2317/622; C07K 2317/76; A61P 35/00; A61K 2039/505
See application file for complete search history.

(56) References Cited

U.S. PATENT DOCUMENTS

| | | |
|---|---|---|
| 5,173,168 A | 12/1992 | Van Haastrecht et al. |
| 5,731,168 A | 3/1998 | Carter et al. |
| 5,869,046 A | 2/1999 | Presta et al. |
| 8,354,509 B2 | 1/2013 | Carven et al. |
| 8,372,396 B2 | 2/2013 | Andya et al. |
| 9,562,109 B2 | 2/2017 | Von Kreudenstein et al. |
| 9,574,010 B2 | 2/2017 | Spreter Von Kreudenstein et al. |
| 9,732,155 B2 | 8/2017 | Spreter Von Kreudenstein et al. |
| 9,758,805 B2 | 9/2017 | De Kruif et al. |
| 9,914,785 B2 | 3/2018 | Corper et al. |
| 9,988,460 B2 | 6/2018 | Spreter Von Kreudenstein et al. |
| 10,344,050 B2 | 7/2019 | Gramer et al. |
| 2006/0074225 A1 | 4/2006 | Chamberlain et al. |
| 2006/0280747 A1 | 12/2006 | Fuh et al. |
| 2013/0195849 A1 | 8/2013 | Spreter Von Kreudenstein et al. |
| 2013/0336981 A1 | 12/2013 | De Kruif et al. |
| 2015/0203579 A1 | 7/2015 | Papadopoulos et al. |
| 2015/0210769 A1 | 7/2015 | Freeman et al. |
| 2016/0193334 A1 | 7/2016 | Strack et al. |
| 2019/0010232 A1 | 1/2019 | Kalos et al. |
| 2019/0284299 A1 | 9/2019 | Liu et al. |

(Continued)

FOREIGN PATENT DOCUMENTS

| | | |
|---|---|---|
| CN | 1299370 A | 6/2001 |
| CN | 103429620 A | 12/2013 |

(Continued)

OTHER PUBLICATIONS

Albanell et al Drugs of today, 35: 931, 1999 (Year: 1999).*
Anja Loffler, et al., "A recombinant bispecific single-chain antibody, CD19 X CD3, induces rapid and high Lymphoma-directed cytotoxicity by unstimulated T lymphocytes", Blood, Mar. 15, 2000, pp. 2098-2103, vol. 95, No. 6.
Ashley Mentlik James, et al., "Combination immune therapies to enhance anti-tumor responses by NK cells", Frontiers in Immunology, Dec. 23, 2013, 12 pages, vol. 4, Art. 481.
Atwell et al., "Stable Heterodimers from Remodeling the Domain Interface of a Homodimer using a Phage Display Library", J. Mol. Biol., 1997, vol. 270, pp. 26-35 (10 pages total).

(Continued)

*Primary Examiner* — Lei Yao
(74) *Attorney, Agent, or Firm* — Sughrue Mion, PLLC

(57) ABSTRACT

Provided are an anti-PD-1/anti-HER2 natural antibody structural heterodimeric bispecific antibody and a method of preparing the same. More particularly, provided are a highly stable heterodimeric anti-PD-1/anti-HER2 bispecific antibody having natural IgG characteristics without mismatch between a heavy chain and a light chain, and a method of preparing the same. The bispecific antibody may bind to two target molecules simultaneously and has excellent effects in treatment of a complex disease.

9 Claims, 16 Drawing Sheets

Specification includes a Sequence Listing.

(56) References Cited

U.S. PATENT DOCUMENTS

| | | |
|---|---|---|
| 2019/0367633 A1 | 12/2019 | Liu et al. |
| 2020/0299412 A1 | 9/2020 | Liu et al. |
| 2021/0040193 A1 | 2/2021 | Yang et al. |
| 2021/0230277 A1 | 7/2021 | Liu et al. |

FOREIGN PATENT DOCUMENTS

| | | | |
|---|---|---|---|
| CN | 104080811 A | 10/2014 | |
| CN | 104114579 A | 10/2014 | |
| CN | 104520320 A | 4/2015 | |
| CN | 105111314 A | 12/2015 | |
| CN | 105175545 A | 12/2015 | |
| CN | 105828837 A | 8/2016 | |
| CN | 106883297 A | 6/2017 | |
| CN | 107198773 A | 9/2017 | |
| CN | 107325184 A | 11/2017 | |
| EP | 3 533 804 A1 | 9/2019 | |
| JP | 2010-530753 A | 9/2010 | |
| JP | 2014-530891 A | 11/2014 | |
| JP | 2014-533243 A | 12/2014 | |
| JP | 2016-508117 A | 3/2016 | |
| WO | 96/27011 A1 | 9/1996 | |
| WO | 99/57134 A1 | 11/1999 | |
| WO | 2004/091658 A1 | 10/2004 | |
| WO | 2009/089004 A1 | 7/2009 | |
| WO | 2010/102241 A1 | 9/2010 | |
| WO | 2010/121766 A1 | 10/2010 | |
| WO | 2011/063348 A1 | 5/2011 | |
| WO | 2012/058768 A1 | 5/2012 | |
| WO | 2012/131555 A2 | 10/2012 | |
| WO | 2012/145493 A1 | 10/2012 | |
| WO | 2013/060867 A2 | 5/2013 | |
| WO | 2013/063702 A1 | 5/2013 | |
| WO | 2013/157953 A1 | 10/2013 | |
| WO | 2013/157954 A1 | 10/2013 | |
| WO | 2014/049003 A1 | 4/2014 | |
| WO | 2014/067011 A1 | 5/2014 | |
| WO | 2014/087248 A2 | 6/2014 | |
| WO | 2015/095404 A2 | 6/2015 | |
| WO | 2015/095412 A1 | 6/2015 | |
| WO | 2015/095418 A1 | 6/2015 | |
| WO | WO-2015095418 A1 * | 6/2015 | ........... A61K 31/282 |
| WO | 2016/024021 A1 | 2/2016 | |
| WO | 2016/057933 A1 | 4/2016 | |
| WO | 2016/109415 A1 | 7/2016 | |
| WO | 2016/115274 A1 | 7/2016 | |
| WO | 2016/170039 A1 | 10/2016 | |
| WO | 2016/201051 A1 | 12/2016 | |
| WO | 2017/024465 A1 | 2/2017 | |
| WO | 2017/101828 A1 | 6/2017 | |
| WO | 2017/117179 A1 | 7/2017 | |
| WO | 2017/167919 A1 | 10/2017 | |
| WO | 2018/002339 A1 | 1/2018 | |
| WO | 2018/068336 A1 | 4/2018 | |
| WO | 2018059502 A1 | 4/2018 | |
| WO | WO-2018068336 A1 * | 4/2018 | ........... A61K 39/395 |
| WO | 2018/090950 A1 | 5/2018 | |
| WO | 2019/068302 A1 | 4/2019 | |
| WO | 2019/153200 A1 | 8/2019 | |

OTHER PUBLICATIONS

Brekken et al., "Selective inhibition of Vascular Endothelial Growth Factor (VEGF) Receptor 2 KKDR/Fik-1) Activity by a Monoclonal Anti-VEGF Antibody Blocks Tumor Growth in Mice", Cancer Research, 60, Sep. 15, 2000, pp. 5117-5124.
Brinkmann, Ulrich, "The making of bispecific antibodies", MABS, vol. 9, No. 2, (Jan. 10, 2017), 182-212.
Bruns et al., "Effect of the Vascular Endothelial Growth Factor Receptor-2 Antibody DC101 Plus Gemcitabine on Growth, Metastasis and Angiogenesis of Human Pancreatic Cancer Growth Orthoropically in Nude Mice", Int. J. Cancer, 2002, 102, pp. 101-108.
Camilla De Nardis et al., "A new approach for generating bispecific antibodies based on a common Tight chain format and the stable architecture of human immunoglobulin G1", J. Biol. Chem., 2017, vol. 292, No. 35, p. 14706-14717 (13 pages total).
Chen et al., "Molecular Pathways: Next Generation Immunotherapy—Inhibiting Programmed Death-Ligand 1 and Programmed Death-1", Clin. Cancer Res., Dec. 15, 2012, 18(24), pp. 6580-6587, 9 pages.
Chen, Lieping, et al., "Anti-PD-1/PD-L1 therapy of human cancer: past, present, and future", The Journal of Clinical Investigation, 125(9), (Sep. 2015), 3384-3391.
Christopher Wright, et al., "Expression of c-erbB-2 Oncoprotein: A Prognostic Indicator in Human Breast Cancer", Cancer Research, Apr. 15, 1989, pp. 2087-2090, vol. 49.
Cornelia Haas, et al., "Mode of cytotoxic action of T cell-engaging BiTE antibody MT110", Immunobiology, 2009, pp. 441-453, vol. 214.
Dennis J. Slamon, et al., "Human Breast Cancer: Correlation of Relapse and Survival with Amplification of the HER-2/neu Oncogene", Science, Jan. 9, 1987, pp. 177-182, vol. 235.
DJ Slamon, et al., "Use of chemotherapy plus a monoclonal antibody against HER2 for metastatic breast cancer that overexpresses HER2", New England Journal of Medicine, Mar. 15, 2001, 4 pp. 783-792, vol. 344, No. 11.
Drew M. Pardoll, "The blockade of immune checkpoints in cancer immunotherapy", Nature, Apr. 2012, pp. 252-264, vol. 12.
Ecuadorean Intellectual Property Office; Communication dated Oct. 8, 2019 issued in counterpart application No. SENADI-2019-22190.
Elena Gianchecci, et al., "Recent insights into the role of the PD-1/PD-L1 pathway in immunological tolerance and autoimmunity", Autoimmunity Reviews, 2013, pp. 1091-1100, vol. 12.
Extended European Search Report dated Dec. 7, 2020 in European Application No. 18777419.5.
F. Revillion, et al., "ERBB2 Oncogene in Human Breast Cancer and its Clinical Significance", European Journal of Cancer, 1998, pp. 791-808, vol. 34, No. 6.
Ferrara et al., "The Biology of VEGF and its Receptors", Angiogenesis Focus, Nature Medicine, vol. 9 No. 6, Jun. 2003, pp. 669-676.
Folkman, J., "Angiogenesis: An Organizing Principle for Drug Discovery?", Nature Reviews, Drug Discovery, vol. 6, Apr. 2007, pp. 273-286.
Folkman, J., "Clinical Applications of Research on Angiogenesis", New England Journal of Medicine, Seminars in Medicine of the Beth Israel Hospital, Boston, vol. 333, No. 26, Dec. 28, 1995, pp. 1757-1763.
Gasparini et al., "Clinical Importance of the Determination of Tumor Angiogenesis in Breast Carcinoma Much More Than a New Prognostic Tool", Journal of Clinical Oncology, vol. 13, No. 3, Mar. 1995, pp. 765-782.
Greg T. Motz, et al., "Deciphering and Reversing Tumor Immune Suppression", Immunity Review, Jul. 25, 2013, pp. 61-73, vol. 39.
Gunasekaran K et al., Enhancing Antibody Fc Heterodimer Formation Through Electrostatic Steering Effects: Applications to Bispecific Molecules and Monovalent IgG J Biol Chem., Apr. 16, 2010, vol. 285, No. 25, pp. 19637-19646 (10 Pages).
Ha, Ji-Hee, "Immunoglobulin Fc Heterodimer Platform Technology: From Design to Applications in Therapeutic Antibodies and Proteins", Frontiers in Immunology, vol. 7, (Oct. 6, 2016), 1-16.
Hartkopf, Andreas D., et al., "PD-1 and PDL1 immune Checkpoint Blockade to Treat Breast Cancer", Breast Care, vol. 11, No. 6, (Jan. 1, 2016), 385-390.
Henick et al., "The PD-1 Pathway as a Therapeutic Target to Overcome Immune Escape Mechanisms in Cancer" Expert Opin. Then Targets, (2014),18(12), 14 pages.
Hye-Ji Choi, et al., "Engineering of Immunoglobulin Fc Heterodimers Using Yeast Surface-Displayed Combinatorial Fc Library Screening", PLOS One, Dec. 16, 2015, vol. 10, No. 12.
"IMGT/2Dstructure-DB card for INN 9798", © Copyright 1995-2015 IMGT © [online], [archived on Apr. 25, 2015], Retrieved from the Internet: <URL: www.imgt.org/3Dstructure-DB/cgi/details.Ggi?pdbcode=9798>, (2015), 2 pgs.
International Search Report and Written Opinion for International Application PCT/CN2019/074541, dated Apr. 30, 2019, 24 pages.
International Search Report for PCT/CN2017/104044 dated Jan. 8, 2018 [PCT/ISA/210].

(56) References Cited

OTHER PUBLICATIONS

International Search Report for PCT/CN2017/111310 dated Feb. 22, 2018 [PCT/ISA/210].
International Search Report for PCT/CN2018/118800 dated Mar. 4, 2019 [PCT/ISA/210].
International Search Report dated Jun. 21, 2018 in International Application No. PCT/CN2018/080858.
Johnson et al., "Randomized Phase II Trial Comparing Bevacizumab Plus Carboplatin and Paclitaxel With Carboplatin and Paclitaxel Alone in Previously Untreated Locally Advanced or Metastatic Non-Small-Cell Lung Cancer", Journal of Clinical Oncology, vol. 22, No. 11, Jun. 1, 2004, pp. 2184-2191.
Kabbinavar et al., "Phase II, Randomized Trial Comparing Bevacizumab Plus Fluorouracil KFU)/Leucovorin (LV) With FU/LV Alone in Patients with Metastatic Colorectal Cancer", J. Clin. Oncol., vol. 21, No. 1, Jan. 1, 2003, pp. 60-65.
Kim C. Ohaegbulam, et al., "Human cancer immunotherapy with antibodies to the PD-1 and PD-L1 pathway", Trends Mol Med, Jan. 2015, 23 pages, vol. 21, No. 1.
Kim et al., "Prospects for Targeting PD-1 and PD-L1 in Various Tumor Types", Oncology Journal, Nov. 11, 2014 Vol. 28, Issue 11,12 pages.
Kumar et al., "Breast Carcinoma: Vascular Density Determined Using CD105 Antibody Correlates with Tumor Prognosis", Cancer Research, 59, Feb. 15, 1999, pp. 856-861.
Liu Boning, " Construction and anti-tumor effects of a new novel bispecific fusion protein targeting pd-L1 and cd47", South China University of Technology, 122 pages (2016).
Liu et al., "Fc Engineering for Developing Therapeutic Bispecific Antibodies and Novel Scaffolds", Frontiers in Immunology, Jan. 2017, vol. 8, Article 38, 15 pages.
Mellman, I., "The Renaissance of Immunotherapy is a Revolution for Cancer Patients", ASCO, GU 2015, 29 pages.
Michaela. Postow, et al., "Immune Checkpoint Blockade in Cancer Therapy", Journal of Clinical Oncology, Jun. 10, 2015, pp. 1974-1982, vol. 33, No. 17.
Michael Jager, et al., Immunomonitoring Results of a Phase II?-III Study of Malignant Ascites Patients Treated with the Trifunctional Antibody Catumaxomab (Anti-EpCAM) x Anti-CD3), Cancer Research, Jan. 1, 2012, pp. 24-32, vol. 72, No. 1.
Pilotto et al., "Immune Checkpoint Inhibitors for Non-small-cell Lung Cancer: Does that Represent a 'New Frontier1?", Anti-Cancer Agents in Medicinal Chemistry, 2015, vol. 15, No. 3, 7 pages.
Pyzik, Michal, et al., "FcRn: The Architect Behind the Immune and Nonimmune Functions of IgG and Albumin", The Journal of Immunology, vol. 194, 2015, pp. 4595-4603 (10 pages).
Roopenian, Derry, et al., "FcRn: the neonatal Fc receptor comes of age", Nature Reviews Immunology, vol. 7, 2007, pp. 715-725.
Sehar Afreen, et al., "The immunoinhibitory B7 H1 molecule as a potential target in cancer: Killing many birds with one stone", Hematol Oncol Stem Cell, First Quarter 2014, 17 pages, vol. 7, No. 1.
Shaheen et al., "Inhibited Growth of Colon Cancer Carcinomatosis by Antibodies to Vascular Endothelial and Epidermal Growth Factor Receptors", British Journal of Cancer, (2001), 85(4), pp. 584-589.
Sockolosky et al., "Durable antitumor responses to CD47 blockade require adaptive immune stimulation", PNAS, 113(19): E2646-E2654 (2016).
Sockolosky, Jonathan, et al., "The neonatal Fc receptor, FcRn, as a target for drug delivery and therapy", Advanced Drug Delivery Reviews, 2014, pp. 1-16.
Stapleton, Nigel, et al., "The multiple facets of FcRn in immunity", Immunological Reviews, 2015, vol. 268, pp. 253-268.
Tartour et al., "Angiogenesis and Immunity: A Bidirectional Link Potentially Relevant for the Monitoring of Antiangiogenic Therapy and the Development of Novel Therapeutic Combination with Immunotherapy", Cancer Metastasis Rev., (2011), 30, pp. 83-95.
Tischer et al., "The Human Gene for Vascular Endothelial Growth Factor", The Journal of Biological Chemistry, vol. 266, No. 18, Jun. 25, 1991, pp. 11947-11954.

Von Kreudenstein et al., "Improving biophysical properties of a bispecific antibody scaffold to aid developability", mAbs, 5(5): 646-654 (2013).
Ward, Sally, et al., "Targeting FcRn for the modulation of antibody dynamics", Molecular Immunology, 2015, pp. 1-11.
Written Opinion for PCT/CN2017/104044 dated Jan. 8, 2018 [PCT/ISA/237].
Written Opinion dated Jun. 21, 2018 in International Application No. PCT/CN2018/080858.
Yasuda et al., "Simultaneous Blockade of Programmed Death 1 and Vascular Endothelial Growth Factor Receptor 2 (VEGFR2) Induces Synergistic Anti-tumour Effect In Vivo", British Society for Immunology, Clinical and Experimental Immunology, 2013, 172, pp. 500-506.
Written Opinion for PCT/IB2019/051008, dated May 29, 2019.
International Search Report for PCT/IB2019/051008, dated May 29, 2019.
Choi et al., "A Heterodimeric Fc-Based Bispecific Antibody Simultaneously Targeting VEGFR-2 and Met Exhibits Potent Antitumor Activity", Molecular Cancer Therapeutics, vol. 12, No. 12, Dec. 2013, pp. 2748-2759 (13 pages total).
Communication dated Sep. 21, 2022 from the Taiwanese Patent Office in Application No. 108103574.
Nihal Tugcu et al., "Maximizing Productivity of Chromatography Steps for Purification of Monoclonal Antibodies", Biotechnology and Bioengineering, Feb. 15, 2008, vol. 99, No. 3, pp. 599-613 (15 pages total).
Brian D. Kelley et al., "Weak Partitioning Chromatography for Anion Exchange Purification of Monoclonal Antibodies", Biotechnology and Bioengineering, Oct. 15, 2008, vol. 101, No. 3, pp. 553-566 (14 pages total).
Richard R. Rustandi et al., "Applications of CE SDS gel in development of biopharmaceutical antibody- based products", Electrophoresis, 2008, vol. 29, pp. 3612-3620 (10 pages total).
Zahra Sharokh et al., "Approaches to Analysis of Aggregates and Demonstrating Mass Balance in Pharmaceutical Protein (Basic Fibroblast Growth Factor) Formulations", Journal of Pharmaceutical Sciences, Dec. 1994, vol. 83, No. 12, pp. 1645-1650 (6 pages total).
Victoria Sluzky et al., "Chromatographic Methods for Quantitative Analysis of Native, Denatured, and Aggregated Basic Fibroblast Growth Factor in Solution Formulations", Pharmaceutical Research, 1994, vol. 11, No. 4, pp. 485-490 (6 pages total).
A.F.M. El Walily et al., Simultaneous determination of tenoxicam and 2-aminopyridine using derivative spectrophotometry and high-performance liquid chromatography, Journal of Pharmaceutical and Biomedical Analysis, 1997, vol. 15, pp. 1923-1928 (6 pages total).
A. Usami et al. "The effect of pH, hydrogen peroxide and temperature on the stability of human monoclonal antibody", Journal of Pharmaceutical and Biomedical Analysis, 1996, vol. 14, pp. 1133-1140 (8 pages total).
Renee Yang et al. High resolution separation of recombinant monoclonal antibodies by size exclusion ultra-high performance liquid chromatography (SE-UHPLC), Journal of Pharmaceutical and Biomedical Analysis, 2015, pp. 1-35 (36 pages total), Accessed via the Internet: http://dx.doi.org/10.1016/j.jpba.2015.02.032.
Alexandre Goyon et al., Protocols for the analytical characterization of therapeutic monoclonal antibodies. I—Non-denaturing chromatographic techniques, Journal of Chromatography B, 2017, pp. 1-30 (31 pages total), Accessed via the Internet: http://dx.doi.org/10.1016/j.jchromb.2017.05.010.
Oscar Salas-Solano et al., "Robustness of iCIEF methodology for the analysis of monoclonal antibodies: An interlaboratory study", J. Sep. Sci. 2012, pp. 3124-3129 (6 pages total).
Oluwatosin O. Dada et al., "Characterization of acidic and basic variants of IgG1 therapeutic monoclonal antibodies based on non-denaturing IEF fractionation", Electrophoresis, 2015, vol. 36, pp. 2695-2702 (8 pages total).
Ann L. Daugherty et al., "Formulation and delivery issues for monoclonal antibody therapeutics", Advanced Drug Delivery Reviews, 2006, vol. 58, pp. 686-706 (21 pages total).

(56) References Cited

OTHER PUBLICATIONS

Wei Wang et al., "Antibody Structure, Instability, and Formulation", Journal of Pharmaceutical Sciences, Jan. 2007, vol. 96, No. 1, pp. 1-26 (26 pages total).

* cited by examiner

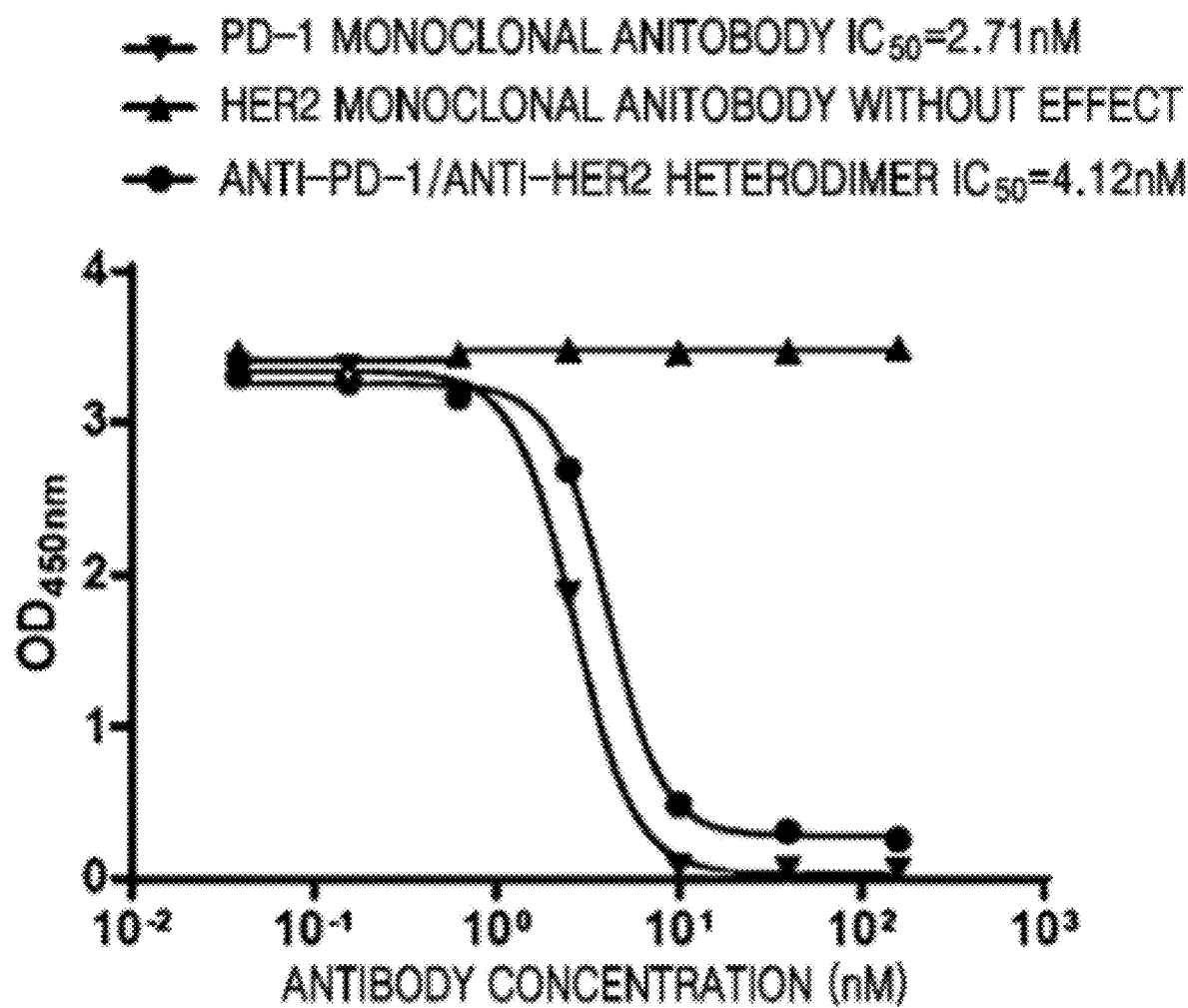

SEQUENCE LISTING

<160> NUMBER OF SEQ ID NOS: 15

<210> SEQ ID NO 1
<211> LENGTH: 321
<212> TYPE: DNA
<213> ORGANISM: Artificial Sequence
<220> FEATURE:
<223> OTHER INFORMATION: Anti-human HER2 antibody light chain variable
      region

<400> SEQUENCE: 1

```
gacattcaga tgactcagag cccttcttca ctgtcagctt ccgtgggcga cagagtcact    60
atcacctgcc gcgcaagtca ggatgtgaac accgcagtcg cctggtacca gcagaagcct   120
ggcaaagctc caaagctgct gatctacagc gcatctttcc tgtattctgg agtgcccagt   180
aggtttagtg ggtcacggtc cggtaccgac ttcacactga ctatctccag cctgcagcct   240
gaggattttg ccacatacta ttgccagcag cactatacca cccccctac tttcggccag    300 ggaaccaaag tggagatcaa g                                             321
```

<210> SEQ ID NO 2
<211> LENGTH: 107
<212> TYPE: PRT
<213> ORGANISM: Artificial Sequence
<220> FEATURE:
<223> OTHER INFORMATION: Anti-human HER2 antibody light chain variable
      region

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 3
<211> LENGTH: 321
<212> TYPE: DNA
<213> ORGANISM: Artificial Sequence
<220> FEATURE:
<223> OTHER INFORMATION: Anti-human HER2 antibody light chain variable
      region

<400> SEQUENCE: 3

```
cgaactgtgg ccgctccaag cgtcttcatt tttccaccct ctgacgaaca gctgaagtca    60
gggacagctt ccgtggtctg tctgctgaac aattttttacc ccaggaggc caaagtgcag   120 tggaaggtcg ataacgctct gcagagcgga aattctcagg agagtgtgac agaacaggac   180
tcaaaagatt ccacttatag cctgtctagt accctgacac tgtccaaggc agactacgaa   240
aagcataaag tgtatgcctg tgaggtcaca catcagggtc tgtcaagccc cgtcactaag   300
tccttcaatc gtggcgaatg c                                             321
```

<210> SEQ ID NO 4
<211> LENGTH: 107
<212> TYPE: PRT
<213> ORGANISM: Artificial Sequence
<220> FEATURE:
<223> OTHER INFORMATION: Anti-human HER2 antibody light chain variable
      region

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 360
<212> TYPE: DNA
<213> ORGANISM: Artificial Sequence
<220> FEATURE:
<223> OTHER INFORMATION: Anti-human HER2 antibody heavy chain variable
      region

<400> SEQUENCE: 5
gaggtgcagc tggtcgaaag tgggggtggg ctggtgcagc caggcggatc actgaggctg        60
tcctgcgccg ctagcggctt caacatcaaa gacacctata ttcactgggt ccgacaggca       120
ccagggaagg gtctggaatg ggtggctcgt atctacccta caaatggtta cactagatat       180
gccgactccg tgaaaggccg gtttactatt tctgctgata ccagtaagaa cacagcatac       240
ctgcagatga atagcctgag ggctgaggat accgcagtgt actattgctc tcggtggggg       300
ggtgacggct tctacgctat ggattattgg ggccagggaa ctctggtcac cgtgtccagc       360

<210> SEQ ID NO 6
<211> LENGTH: 120
<212> TYPE: PRT
<213> ORGANISM: Artificial Sequence
<220> FEATURE:
<223> OTHER INFORMATION: Anti-human HER2 antibody heavy chain variable
      region

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 7
<211> LENGTH: 990
<212> TYPE: DNA
<213> ORGANISM: Artificial Sequence
<220> FEATURE:
<223> OTHER INFORMATION: Anti-human HER2 antibody heavy chain constant
      region

<400> SEQUENCE: 7
gcttcaacaa aaggaccttc cgtgtttcca ctggcaccct ctagtaagag tacttcagga    60
ggaaccgcag cactgggatg tctggtgaag gactacttcc cagagcccgt caccgtgtct   120
tggaacagtg gagcactgac ctccggggtc catacatttc ctgccgtgct gcagtcatcc   180
ggtctgtata gcctgagctc tgtggtcaca gtcccaagtt catccctggg cacccagaca   240
tacatctgca acgtgaatca caaaccttcc aatactaagg tcgacaagaa agtggaacca   300
aaaagctgtg ataagactca tacctgccca ccttgtcctg caccagagct gctgggaggt   360
ccaagcgtgt tcctgtttcc acccaagccc aaagacacac tgatgatttc tcgcacaccc   420
gaagtcactt gtgtggtcgt ggacgtgtcc cacgaggatc ctgaagtcaa gttcaactgg   480
tacgtggatg gcgtcgaggt gcataatgct aagaccaaac ccagagagga acagtacaac   540
agcacctatc gcgtcgtgtc tgtcctgaca gtgctgcacc aggattggct gaacggaaag   600
gagtacaagt gcaaagtgag caacaaggcc ctgcccgctc tatcgagaa gaccatttct   660 aaggctaaag gccagcctag agaaccacag gtgtatacag agcctccaag tcgcgacgag   720
ctgacaaaaa accaggtctc cctgacttgt ctggtgaagg gattctaccc tagcgatatc   780
gcagtggagt gggaatctaa tgggcagcca gaaaacaatt ataagaccac ccccctgtg    840 ctggactcag atggttcctt ctttctgctg agtgtgctga ccgtggacaa gtccaggtgg   900
cagcagggga acgtctttc ctgcagcgtg atgcatgagg ccctgcacaa tcattacaca   960
cagaaatctc tgagtctgtc accaggaaag                                    990

<210> SEQ ID NO 8
<211> LENGTH: 330
<212> TYPE: PRT
<213> ORGANISM: Artificial Sequence
<220> FEATURE:
<223> OTHER INFORMATION: Anti-human HER2 antibody heavy chain constant
      region

<400> SEQUENCE: 8

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Glu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Leu Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 321
<212> TYPE: DNA
<213> ORGANISM: Artificial Sequence
<220> FEATURE:
<223> OTHER INFORMATION: Anti-human HER2 antibody light chain variable
      region

<400> SEQUENCE: 9
gacatccaga tgacccagtc ccctagcagc gtgagcgctt ccgtgggcga cagggtgacc      60
atcacctgca gggcctccca gggcatctcc tcctggctgg cctggtatca acagaagccc    120
ggcaaggccc ccaagctgct gatctccgct gcctcctccc tgcagtccgg agtgccttcc    180
aggttcagcg gttctggctc cggcaccgac ttcaccctga ccatctcctc cctgcagccc    240
gaggacttcg ccacctacta ctgccagcag gccaaccacc tgcctttcac cttcggcggc    300
ggcaccaagg tggagatcaa g                                              321

<210> SEQ ID NO 10
<211> LENGTH: 107
<212> TYPE: PRT
```

<213> ORGANISM: Artificial Sequence
<220> FEATURE:
<223> OTHER INFORMATION: Anti-human HER2 antibody light chain variable
      region

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
            100                 105

<210> SEQ ID NO 11
<211> LENGTH: 360
<212> TYPE: DNA
<213> ORGANISM: Artificial Sequence
<220> FEATURE:
<223> OTHER INFORMATION: Anti-human HER2 antibody heavy chain variable
      region

<400> SEQUENCE: 11
caggtgcagc tggtgcagtc cggagccgag gtgaagaagc ccggctcctc cgtgaaggtg      60
tcctgcaagg cctccggcgg caccttctcc tccaccgcca tctcctgggt gaggcaggct     120
cctggccagg gactggagtg gatgggaggc atctggccct ccttcggcac agcctcctac     180
gcccagaagt tccagggcag ggtgaccatc accgccgacg agagcacctc caccgcctac     240
atggagctga gctccctgag gtccgaggac accgccgtgt actactgtgc agggccgag      300 tactcctcca ccggcatctt cgactactgg ggccagggca ccctggtgac agtgtcctcc     360

<210> SEQ ID NO 12
<211> LENGTH: 120
<212> TYPE: PRT
<213> ORGANISM: Artificial Sequence
<220> FEATURE:
<223> OTHER INFORMATION: Anti-human HER2 antibody heavy chain variable
      region

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Thr
            20                  25                  30

Ala Ile Ser Trp Val Arg Gln Ala Pro Gly Gln Gly Leu Glu Trp Met
        35                  40                  45

Gly Gly Ile Trp Pro Ser Phe Gly Thr Ala Ser Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu Tyr Ser Ser Thr Gly Ile Phe Asp Tyr Trp Gly Gln
            100                 105                 110

Gly Thr Leu Val Thr Val Ser Ser
        115                 120

<210> SEQ ID NO 13
<211> LENGTH: 990
<212> TYPE: DNA
<213> ORGANISM: Artificial Sequence
<220> FEATURE:
<223> OTHER INFORMATION: Anti-human HER2 antibody heavy chain constant
      region

<400> SEQUENCE: 13
gcttcaacaa aaggaccttc cgtgtttcca ctggcaccct ctagtaagag tacttcagga      60
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaacca    300
aaaagctgtg ataagactca tacctgccca ccttgtcctg caccagagct gctgggaggt    360
ccaagcgtgt tcctgtttcc acccaagccc aaagacacac tgatgatttc tcgcacaccc    420
gaagtcactt gtgtggtcgt ggacgtgtcc acgaggatc tgaagtcaa gttcaactgg    480 tacgtggatg gcgtcgaggt gcataatgct aagaccaaac ccagagagga acagtacaac    540
agcacctatc gcgtcgtgtc tgtcctgaca gtgctgcacc aggattggct gaacggaaag    600
gagtacaagt gcaaagtgag caacaaggcc ctgcccgctc ctatcgagaa gaccatttct    660
aaggctaaag gccagcctag agaaccacag gtgtatacac tgcctccaag tcgcgacgag    720
ctgacaaaaa accaggtctc cctgctgtgt ctggtgaagg gattctaccc tagcgatatc    780
gcagtggagt gggaatctaa tgggcagcca gaaacaatt ataagaccac ccccctgtg    840 ctgcggtcag atggttcctt ctttctgtac agtaaactga ccgtggacaa gtccaggtgg    900
cagcagggga acgtctttc ctgcagcgtg atgcatgagg ccctgcacaa tcattacaca    960
cagaaatctc tgagtctgtc accaggaaag                                    990

<210> SEQ ID NO 14
<211> LENGTH: 330
<212> TYPE: PRT
<213> ORGANISM: Artificial Sequence
<220> FEATURE:
<223> OTHER INFORMATION: Anti-human HER2 antibody heavy chain constant
      region

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
                      85                  90                  95
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Arg Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 15
<212> TYPE: DNA
<213> ORGANISM: Artificial Sequence
<220> FEATURE:
<223> OTHER INFORMATION: linker

<400> SEQUENCE: 15
ggggsggggs ggggs                                                    15
```

ANTI-PD-1/ANTI-HER2 NATURAL ANTIBODY STRUCTURAL HETERODIMERIC BISPECIFIC ANTIBODY AND METHOD OF PREPARING SAME

CROSS REFERENCE TO RELATED APPLICATIONS

This application is a National Stage of International Application No. PCT/IB2019/051008 filed Feb. 8, 2019, claiming priority based on International Patent Application No. PCT/CN2018/075851 filed Feb. 8, 2018.

SEQUENCE LISTING

The content of the electronically submitted sequence listing, file name: Substitute_Sequence_Listing_As_Filed.txt; size: 17,933 bytes; and date of creation: Aug. 18, 2022, filed herewith, is incorporated herein by reference in its entirety.

PARTIES TO A JOINT RESEARCH AGREEMENT

The subject matter disclosed in U.S. Pat. No. 11,319,378 (application Ser. No. 16/461,646) was developed by and the claimed invention was made by or on behalf of, one or more parties to a joint research agreement that was in effect on or before the effective filing date the claimed invention, and the claimed invention was made as a result of activities undertaken within the scope of the joint research agreement. The parties to the joint research agreement are BEIJING HANMI PHARMACEUTICAL CO., LTD. and INNOVENT BIOLOGICS (SUZHOU) CO., LTD.

TECHNICAL FIELD

The present disclosure relates to an anti-PD-1/anti-HER2 natural antibody structural heterodimeric bispecific antibody and a method of preparing the same, and more particularly, to a highly stable heterodimeric anti-PD-1/anti-HER2 bispecific antibody having natural IgG characteristics without mismatch between a heavy chain and a light chain, and a method of preparing the same.

BACKGROUND ART

Monoclonal antibodies are highly specific antibodies that act only on a single antigenic epitope and have been widely used in the treatment of many diseases, such as cancer, inflammatory diseases, autoimmune diseases, and infectious diseases. However, when such a therapeutic molecule is used alone, the therapeutic molecule is not capable of exhibiting sufficient efficacy. This may result from the complexity of a disease. For example, cancer or inflammatory diseases typically involve a variety of disease-mediated molecular pathways of and interphase action between signal pathways. In these cases, a molecule that targets a single target may provide an optimal therapeutic effect. By simultaneously blocking multiple targets or blocking molecules at multiple sites of a target, a therapeutic effect may be improved. As a multispecific molecule, e.g., a bispecific molecule, is a single molecule, the multispecific molecule may enable a dual-targeted therapy and simplify a development process of a new drug. Using a multispecific molecule is more convenient for both patients and medical service providers than using a combination of multiple monospecific molecules.

Many different types of bispecific antibodies or bifunctional molecules have been reported in the art. The first bispecific antibody was prepared by using a chemical method using a bifunctional coupling reagent for joining an IgG molecule to a Fab' or (Fab')2 fragment. However, such a chemically coupled bispecific antibody may have a number of limitations, such as labor intensity of production, purification of heterologous conjugates or homologous conjugates, and complexities in removal of an original monoclonal antibody or a fragment thereof; and a low yield.

Another method of generating a bispecific antibody is to use hybrid-hybridoma (or four-source hybridoma) technology, which employs somatic cell fusion of two hybridoma cell lines that secrete different antibodies. Due to random pairing of immunoglobulin heavy and light chains, only 1/10 of the antibody is the desired functional bispecific antibody, which thus may complicate the purification process and reduce a production yield.

WO 2013/060867 discloses a large-scale production method of a heterodimeric bispecific antibody. In the method, first, two mixed homodimeric antibodies are reduced. Then, an asymmetric amino acid mutation is introduced into CH3 regions of the two homodimeric antibodies to facilitate the Fab-arm exchange between different antibodies. Finally, a stable bispecific antibody is formed by oxidization of an inter-chain disulfide bond in a hinge region.

WO 2009/089004 discloses a method for making a heterodimeric protein. In the method, an amino acid at a CH3-CH3 interface is mutated into a charged amino acid to promote formation of a heterodimer by electrostatic action. However, this method is unfavorable for formation of a homodimer.

U.S. Pat. No. 5,731,168 discloses a method of preparing a heterodimeric IgG using a "protuberance-cavity" strategy. In the method, "protuberances" are constructed by replacing small amino acid side chains from the interface of the CH3 domain of the first polypeptide with larger amino acid side chains, and compensatory "cavities" are created in the interface of the CH3 domain of the second polypeptide by replacing large amino acid side chains with smaller amino acid side chains. The interaction between protuberances and cavities facilitates formation of heterodimeric IgG and is not effective in formation of homodimers.

WO 2012/058758 discloses a method of preparing a highly specific stable heterodimeric IgG. The method combines both negative and positive design strategies along with structural and computational modeling guided protein engineering techniques and allows novel combinations of mutations in the IgG1 CH3 domain to be designed, thereby forming a stable heterodimeric IgG with a small amount of homodimer impurities.

The programmed death receptor-1 (PD-1) has recently received attention as an immune checkpoint that is involved in the regulation of T cell activation and regulates the strength and duration of immune responses. Under normal circumstances, PD-1 may mediate and maintain the autoimmune tolerance of tissues of organisms and prevent excessive activation of an immune system during an inflammatory reaction and damage of its own tissues, thus providing a positive effect. However, under pathologic circumstances, PD-1 is involved in the occurrence and development of various tumors and autoimmune diseases (Anticancer Agents Med Chem. 2015; 15(3):307-13. Hematol Oncol Stem Cell Ther. 2014 March; 7(1):1-17. Trends Mol Med. 2015 January; 21(1):24-33. Immunity. 2013 Jul. 25; 39(1): 61-73. J Clin Oncol. 2015 Jun. 10; 33(17):1974-82.).

PD-1 belongs to the CD28 family, but unlike other members of the CD28 family, e.g., CTLA4, which may form a covalent dimer with a disulfide bond, PD-1 exists as a monomer. The structure of PD-1 mainly includes an extracellular immunoglobulin variable region-like domain, a hydrophobic transmembrane domain, and an intracellular domain, and the intracellular domain contains two independent phosphorylation sites, which are an immunoreceptor tyrosine-based inhibition motif (ITIM) and an immunoreceptor tyrosine-based switch motif (ITSM), respectively. PD-1 is mainly induced to be expressed on a surface of activated T cells, and is also expressed in B cells, NK cells, monocytes, and DC cells. The ligands of PD-1 includes programmed death ligand 1 (PD-L1) and programmed death ligand 2 (PD-L2), and the ligands belong to the B7 family, in which PD-L1 is induced to be expressed on surfaces of various immune cells including T cells, B cells, monocytes, macrophages, DC cells, endothelial cells, epidermal cells, and the like, while PD-L2 is only induced to be expressed in some immune cells, including macrophages, DC cells, B cells, and the like (Autoimmun Rev, 2013, 12(11):1091-1100. Front Immunol, 2013, 4:481. Nat Rev Cancer, 2012, 12(4): 252-264. Trends Mol Med. 2015 January; 21(1): 24-33.).

In the 1980s, Denis Slamon first discovered that the HER2 (human epidermal growth factor receptor 2) gene was excessively amplified in 30% of 189 cases of primary breast cancer, and that HER2 is closely related to overall viability and recurrence time (Salman D J et al, Science, 235:177-182, 1985). The current study shows that HER2 is overexpressed in about 25 percent (%) to about 30% of breast cancer patients (Revillion F et al, Eur J Cancer, 34:791-808, 1998), and these studies are associated with a degree of malignant growth of tumors (Wright C et al, Cancer Res, 49: 2087-2090, 1989).

Trastuzumab is an anti-HER2 extracellular domain of a humanized monoclonal antibody (Carter P et al, PNAS, 89(10):4285-4289, 1992). However, the anti-cancer effects of Trastuzumab in clinical applications are not as great as in preclinical experiments. Thus, Trastuzumab is often used in a drug combination with chemotherapy drugs and the like (Slamon D J et al, N Engl J Med, 344:783-792, 2001).

Designing a bifunctional antibody that recruits effector cells is effective in improving antibody performance. So far, the greatest amount of research has been done on the use of the function of a CD3 molecule. The CD3 molecule may effectively remove the target tumor by the activation of killer T cells (Haas C et al, Immunobiology, 214:441-453, 2009). The recombinant bispecific T cell engager (BiTE) developed by Micormet, has good prospects; however, the biggest problem is that the plasma half-life is very short, i.e., only 1 hour of half-life in a human body (Loffler A et al, Blood, 95:2098-2103). This is caused by the structure of BiTE itself, which consists of two single-chain antibody fragments with a molecular weight of only 60 kiloDaltons (kDa) and lacks an Fc fragment that is important for prolonging the half-life in an antibody molecule.

Catumaxomab, which is another promising multi-functional antibody, is a hetero Ig molecule that targets CD3 and EpCAM. Catumaxomab has been approved for the treatment of ascites carcinoma (Jager M et al, Cancer Res, 72:24-32, 2012). Another multi-functional antibody in clinical phase II is Ertumaxomab, which targets CD3 and HER2. A branch of heavy and light chains of the hetero antibody is derived from a rat IgG and targets CD3; and another branch of heavy and light chains thereof is derived from a mouse IgG and targets HER2. The problem of Ertumaxomab is that production thereof is very difficult. The reason for this is that, to obtain a clone expressing the bifunctional Ertumaxomab, a diploid hybridoma expressing a CD3 specific antibody and a diploid hybridoma expressing a HER2-specific antibody are first obtained, and then, the two hybridomas are hybridized again to obtain a bifunctional tetraploid hybridoma which may express anti-CD3 and anti-HER2 bispecificity. The production of a common single target antibody requires only one diploid hybridoma. In contrast, the production of a bifunctional antibody is more complicated, and the production of a tetraploid hybridoma is more difficult since it is sourced from a rat, which may result in high immunogenicity.

In addition, the most apparent side reaction of anti-CD3 antibodies is the increase of cytokines in the body within a short time, also known as cytokine storms. There is therefore a need to develop a new bifunctional antibody that recruits immune cells to tumor cells.

Combined administration requires sequential injection of two or more antibodies or formation of the antibodies in the same dosage form. However, on one hand, sequential injection of antibodies reduces treatment cooperativeness of patients and increases pain. On the other hand, due to the differences in the physicochemical properties of different antibodies, it is difficult or almost impossible to formulate different antibodies into the same dosage form.

In this view, it is still necessary to study a novel therapeutic drug that blocks both PD-1 and HER2 signaling pathways.

DESCRIPTION OF EMBODIMENTS

Technical Problem

The present disclosure relates to a highly stable heterodimeric bifunctional antibody having natural IgG characteristics without mismatch between a heavy chain and a light chain and capable of preventing PD-1 and HER2 simultaneously and a method of preparing the bifunctional antibody. The bifunctional antibody may tend to selectively bind to tumor cells that simultaneously express PD-1 and HER2, thereby exerting a highly effective and specific killing effect with less toxic side effects.

A first aspect of the present disclosure relates to a heterodimeric bispecific antibody. The bispecific antibody may include: a first antigen-binding site capable of specifically binding to PD-1 and a second antigen-binding site capable of specifically binding to HER2, wherein the bispecific antibody may include a first Fc chain and a second Fc chain that may be chain-linked to each other via at least one disulfide bond, wherein the first Fc chain and the second Fc chain may each be linked to a PD-1 antigen-binding site and a HER2 antigen-binding site, respectively, via a covalent bond or a linking group, or the first Fc chain and the second Fc chain may each be linked to a HER2 antigen-binding site and a PD-1 antigen-binding site, respectively, via a covalent bond or a linking group, and an amino acid sequence of an immunoglobulin light chain variable region in the PD-1 antigen-binding site may be the SEQ ID NO:10, an amino acid sequence of an immunoglobulin heavy chain variable region in the PD-1 antigen-binding site is the SEQ ID NO: 12, and the first Fc chain and the second Fc chain may include five substitutions of amino acids at the following positions:

the first Fc chain may include substitutions of amino acids of a 366th amino acid and a 399th amino acid; and the second Fc chain may include substitutions of amino acids of a 351st amino acid, a 407th amino acid, and a 409th amino acid, wherein the first Fc chain and the second Fc chain each including the substitutions of amino acids may have a tendency to together form a heterodimer rather than having a tendency to form a homodimer, wherein amino acid positions may be numbered according to the Kabat EU Index Numbering System.

In some embodiments, the first Fc chain and the second Fc chain substitutions of amino acids may be as follows:
 a) L351G, L351Y, L351V, L351P, L351D, L351E, L351K, or L351W;
 b) T366L, T366P, T366W, or T366V;
 c) D399C, D399N, D399I, D399G, D399R, D399T, or D399A;
 d) Y407L, Y407A, Y407P, Y407F, Y407T, or Y407H; and
 e) K409C, K409P, K409S, K409F, K409V, K409Q, or K409R.

In some embodiments, the substitutions of amino acids may include:
 a) T366L and D399R substitutions of the first Fc chain and L351E, Y407L, and K409V substitutions of the second Fc chain;
 b) T366L and D399C substitutions of the first Fc chain and L351G, Y407L, and K409C substitutions of the second Fc chain;
 c) T366L and D399C substitutions of the first Fc chain and L351Y, Y407A, and K409P substitutions of the second Fc chain;
 d) T366P and D399N substitutions of the first Fc chain and L351V, Y407P, and K409S substitutions of the second Fc chain;
 e) T366W and D399G substitutions of the first Fc chain and L351D, Y407P, and K409S substitutions of the second Fc chain;
 f) T366P and D399I substitutions of the first Fc chain and L351P, Y407F, and K409F substitutions of the second Fc chain;
 g) T366V and D399T substitutions of the first Fc chain and L351K, Y407T, and K409Q substitutions of the second Fc chain; or
 h) T366L and D399A substitutions of the first Fc chain and L351W, Y407H, and K409R substitutions of the second Fc chain.

In some embodiments, amino acids of the first Fc chain are substituted with T366L and D399R, and amino acids of the second Fc chain are substituted with L351E, Y407L, and K409V.

In some embodiments, the Fc chains may be derived from IgG.

In some embodiments, the PD-1 antigen-binding site and the HER2 antigen-binding site may each be a Fab fragment or an scFv fragment.

In some embodiments, the PD-1 antigen-binding site and the HER2 antigen-binding site may each be a Fab fragment.

In some embodiments, one selected from the PD-1 antigen-binding site and the HER2 antigen-binding site may be a Fab fragment, and the other may be an scFv fragment.

In some embodiments, the Fab fragment may include different first and second heavy chain variable regions and different first and second light chain variable regions.

In some embodiments, when each of the first Fc chain covalently bonded to the PD-1 antigen binding region and the second Fc chain covalently bonded to the HER2 antigen binding region, or each of the first Fc chain covalently bonded to the HER2 antigen binding region and the second Fc chain covalently bonded to the PD-1 antigen binding region, is present alone in the presence of a reducing agent, the weight ratio of the constituent homodimers are smaller than 50%.

In some embodiments, an amino acid sequence of the bispecific antibody is selected from the SEQ ID NOs. 2, 4, 6, 8, 10, 12, and 14. In some embodiments, an amino acid sequence of the bispecific antibody is selected from a corresponding combination of the SEQ ID NOs. 2, 4, 6, 8, 10, 12, and 14.

A second aspect of the present disclosure relates to an isolated polynucleotide encoding the heterodimeric bispecific antibody of the first aspect.

In some embodiments, a sequence of the isolated polynucleotide is selected from the SEQ ID NOs. 1, 3, 5, 7, 9, 11, and 13. In some embodiments, a sequence of the isolated polynucleotide is selected from a corresponding combination of the SEQ ID NOs. 1, 3, 5, 7, 9, 11, and 13.

A third aspect of the present disclosure relates to a recombinant plasmid including the isolated polynucleotide of the second aspect.

In some embodiments, an expression vector may be a plasmid vector X0GC modified from pcDNA.

A fourth aspect of the present disclosure relates to a host cell including the isolated polynucleotide of the second aspect or the recombinant expression vector of the third aspect.

In some embodiments, the host cell may be a human embryonic kidney cell HEK293, or HEK293T, HEK293E, or HEK293F modified from a HEK293 cell; or a hamster ovary cell CHO, or CHO-S, CHO-dhfr-, CHO/DG44, or ExpiCHO modified from a CHO cell.

A fifth aspect of the present disclosure relates to a composition including the heterodimeric bispecific antibody of the first aspect, the isolated polynucleotide of the second aspect, the recombinant expression vector of the third aspect, or the host cell of the fourth aspect, and a pharmaceutically acceptable carrier.

A sixth aspect of the present disclosure relates to a method of preparing the heterodimeric bispecific antibody of the first aspect, the method including:
 1) expressing the isolated polynucleotide of the second aspect or the recombinant expression vector of the third aspect in a host cell;
 2) reducing each expressed protein in the host cell; and
 3) mixing the reduced protein and oxidizing the mixture.

In some embodiments, the host cell may be selected from a human embryonic kidney cell HEK293, or HEK293T, HEK293E, or HEK293F modified from a HEK293 cell; and a hamster ovary cell CHO, or CHO-S, CHO-dhfr-, CHO/DG44, or ExpiCHO modified from a CHO cell.

In some embodiments, the reducing may include: 1) performing a reduction using a reducing agent including 2-mercaptoethylamine, dithiothreitol, tris(2-carboxyethyl)phosphine, or a chemical derivative or combination thereof; and 2) removing the reducing agent.

In some embodiments, the oxidizing may be performed in air and include oxidation performed in the presence of an oxidizing agent, the oxidizing agent being selected from L-dehydroascorbic acid and another chemical derivative.

In some embodiments, the method may further include isolation and purification.

A seventh aspect of the present disclosure relates to use of including the heterodimeric bispecific antibody of the first aspect, the isolated polynucleotide of the second aspect, the recombinant expression vector of the third aspect, the host cell of the fourth aspect, and/or the composition of the fifth aspect, in a drug for preventing and/or treating a disease of a subject.

An eighth aspect of the present disclosure relates to the heterodimeric bispecific antibody of the first aspect, the isolated polynucleotide of the second aspect, the recombinant expression vector of the third aspect, the host cell of the fourth aspect, and/or the composition of the fifth aspect used in preventing and/or treating a disease of a subject.

A ninth aspect of the present disclosure relates to a method of preventing and/or treating a disease, the method including: administering the heterodimeric bispecific antibody of the first aspect, the isolated polynucleotide of the second aspect, the recombinant expression vector of the third aspect, the host cell of the fourth aspect, and/or the composition of the fifth aspect to a subject in need thereof.

In some embodiments, the subject may be a mammal, preferably a human.

In some embodiments, the disease is selected from diseases including leukemia, lymphoma, myeloma, brain tumors, head and neck squamous cell carcinoma, non-small cell lung cancer, nasopharyngeal cancer, esophageal cancer, stomach cancer, pancreas cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma.

The present disclosure relates to an anti-PD-1/anti-HER2 natural antibody structural heterodimeric bispecific antibody, wherein the anti-PD-1/anti-HER2 structural heterodimeric bispecific antibody is highly stable and has natural IgG characteristics without mismatch between a heavy chain and a light chain. The bispecific antibody may be capable of binding to target molecules PD-1 and HER2 simultaneously, and is more effective in treating complex diseases.

BRIEF DESCRIPTION OF DRAWINGS

FIGS. 10A and 10B each show that an anti-PD-1/anti-HER2 heterodimeric antibody blocked PD-1/PD-L1 binding and PD-1/PD-L2 binding and better retained the blocking activity of the bivalent monoclonal antibody;

MODE OF DISCLOSURE

Figure 1:
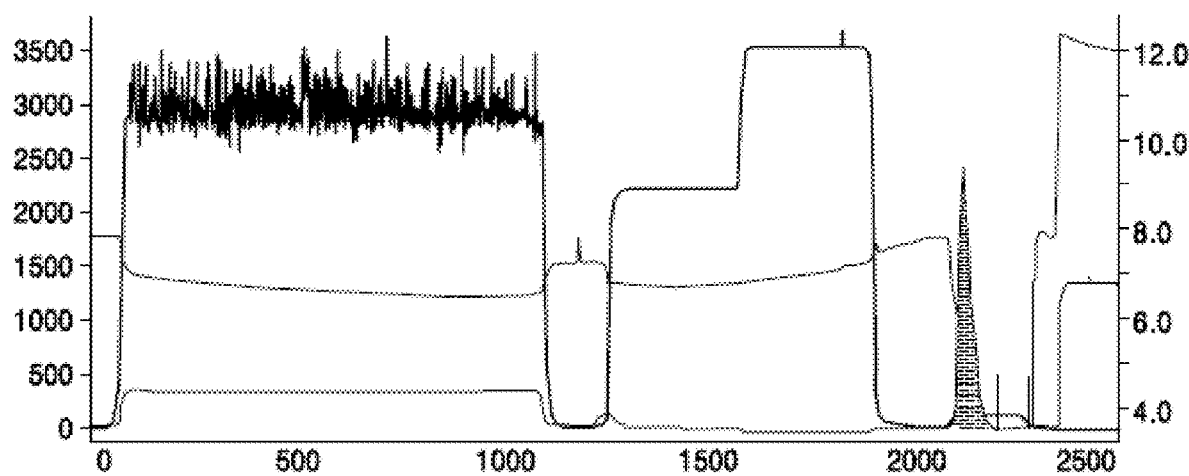
FIG. 1 shows an elution peak chromatogram of the anti-PD-1 expression product.

Definitions:

Covalent linkage refers to binding by a covalent bond between an Fc chain among two Fc chains and an antigen-binding functional site bound thereto in a heterodimeric bispecific antibody, thus binding the Fc chain with the antigen-binding functional site to form a molecule. The Fc chain may include a first antigen-binding site and a second antigen-binding site joined by at least one covalent linkage (e.g., a disulfide bond chain). The first Fc chain and the second Fc chain are each attached to an antigen-binding site by a covalent linkage (e.g., an imine bond or an amide bond). An antigen-binding site refers to a site that may specifically interact with a target molecule such as an antigen. Action thereof is highly selective, and thus a sequence that recognizes one target molecule generally does not recognize other molecular sequences.

Representative antigen-binding sites include: a variable region of an antibody, a structural allosteric variable region of an antibody, a binding domain of a receptor, a ligand binding domain, or an enzyme binding domain.

At least one inter-chain disulfide bond refers to a first Fc chain being linked to a second Fc chain by at least one disulfide bond to form a heterodimeric fragment. In the present disclosure, formation of at least one disulfide bond may be between the first Fc chain and the second Fc chain; or the first Fc chain, the second Fc chain, and an antigen-binding site bound thereto synthesized in the same cell. Also, the first Fc chain and the second Fc chain; or the first Fc chain, the second Fc chain, and an antigen-binding site bound thereto may each be separately synthesized in different cells, and then formed by in vitro reductive oxidation.

The first Fc chain and the second Fc chain may form a binding fragment by covalent linkage, wherein the covalent linkage may include a disulfide bond, each chain includes at least a portion of a constant region in a heavy chain of an immunoglobulin (Ig), and the first Fc chain and the second Fc chain may differ in amino acid sequence and include at least one amino acid difference. In the first Fc chain and the second Fc chain of the present disclosure, a strong mutual repulsion may occur among the same chains, and attraction may occur among the different chains. Thus, when co-expressed in cells, the first Fc chain and the second Fc chain; or the first Fc chain, the second Fc chain, and an antigen-binding site bound thereto are more prone to forming heterodimers. When the first Fc chain and the second Fc chain; or the first Fc chain, the second Fc chain, and an antigen-binding site bound thereto are each expressed in two host cells, respectively, the first Fc chain or the antigen-binding site bound to the first Fc chain may not be prone to forming a homodimer, and the second Fc chain or the antigen-binding site bound to the second Fc chain also may not be prone to forming a homodimer. In the present disclosure, when the first Fc chain and the second Fc chain; or the first Fc chain, the second Fc chain, and an antigen-binding site bound thereto are each expressed in two host cells in the presence of a reducing agent, respectively, a ratio of homodimers may be 50% or less, that is, a ratio of monomers (a single chain of the Fc chain or a single chain of the Fc chain and the antigen-binding site bound thereto) may be greater than 50%.

Immunoglobulin has a symmetrical structure having four polypeptide chains. Two of the four polypeptide chains are the same heavy chain having a relative large molecular weight and 450 to 550 amino acid residues, and a relative molecular weight thereof may be in a range of 55,000 Daltons (Da) to 70,000 Da. The other two of the four polypeptide chains are the same light chain (L chain) having a relatively small molecular weight and 210 amino acid residues, and a relative molecular weight thereof may be about 24,000 Da. The sequence of about 110 amino acids near the N-terminal in the different heavy and light chains of immunoglobulin may greatly vary. Thus, the sequence is referred to as a variable region (V region). The remaining amino acid sequence near the C-terminal is relatively stable. Thus, the remaining sequence is referred to as a constant region (C region). The variable region in the heavy chain accounts for about ¼ of the length of the heavy chain, and the constant region accounts for about ¾ of the length of the heavy chain. The known 5 types of Ig(s) include IgG (γ), IgA (α), IgD (δ), IgM (μ), and IgE (ε). The heavy chain of each of IgG (γ), IgA (α), and IgD (δ) includes three constant regions, namely, CH1, CH2, and C3. The heavy chain of each of IgM (μ) and IgE (ε) includes one variable heavy chain (VH) region and four constant regions, namely, CH1, CH2, CH3, and CH4. The constant region is both the backbone of an immunoglobulin molecule and one of the sites that activate an immune response.

The constant region in the present disclosure may include at least one interaction region of the first Fc chain and the second Fc chain, and the interaction region may be positioned in a portion of amino acids of the CH3 region in IgG, including at least GLN347, TYR349, THR 350, LEU 351, SER 354, ARG 355, ASP 356, GLU 357, LYS 360, SER 364, THR 366, LEU 368, LYS 370, ASN390, LYS392, THR394, PRO395, VAL 397, ASP399, SER400, PHE405, TYR407, LYS409, and LYS439.

The attachment of the first Fc chain and the second Fc chain to an antigen-binding site by a covalent bond or a linker may refer to the first Fc chain and the second Fc chain being respectively linked to an antigen-binding fragment of an antibody by a covalent bond or a linker, wherein the antigen-binding fragment recognizes a single chain antibody that recognizes an antigen, recognizes a receptor of a ligand, or recognizes a ligand of a receptor. The covalent bond is a type of chemical bond in which two or more atoms share outer electrons together, ideally reaching an electronic saturation state, thereby forming a relatively stable chemical structure called a covalent bond. The covalent bond is an interaction formed by sharing electron pairs between atoms. The atoms of the same or different elements may be bound by a covalent bond. The covalent bond between the first Fc chain and the second Fc chain of the present disclosure includes, but not limited to, a peptide bond formed by dehydration between an amino group of a molecule of an amino acid and a carboxyl group of another molecule of an amino acid, or a peptide bond or an imine bond between an aldehyde group of ethylene glycol, polyethylene glycol, another compound, or a multimer thereof and an amino group of a molecule of an amino acid. A linker may be an amino acid sequence, a compound, or a multimer of a compound, in which two polypeptide chains are joined by a covalent bond, wherein the amino acid sequence may include, but not limited to, a small peptide such as GGGGSGGGGSGGGGS (SEQ ID NO: 15), wherein the linker may link, by a peptide bond, the first Fc chain or the second Fc chain with a single chain antibody that may recognize an antigen or with a structural allosteric variant of a fragment of another antibody that may recognize an antigen.

The fact that the first Fc chain and the second Fc chain may be prone to forming a heterodimer and may not be prone to forming a homodimer means that a strong mutual repulsion may occur among the same polypeptide chains, and an attraction may occur among the different polypeptide chains of the first Fc chain and the second Fc chain polypeptide chain, and thus, when co-expressed in cells, the first Fc chain and the second Fc chain; or the first Fc chain, the second Fc chain, and an antigen-binding site bound thereto are more prone to forming heterodimers. When the first Fc chain and the second Fc chain; or the first Fc chain, the second Fc chain, and an antigen-binding site bound thereto are each expressed in two host cells, respectively, the first Fc chain or the antigen-binding site bound to the first Fc chain may not be prone to forming a homodimer, and the second Fc chain or the antigen-binding site bound to the second Fc chain also may not be prone to forming a homodimer.

The Kabat EU Index Numbering System means that Kabat uses a method of numbering each amino acid of an antibody sequence, and this method of numbering each residue has become a standard method in the art. The Kabat protocol may be extended to other antibodies that may not have been studied, and based on conserved amino acids, a target antibody may be aligned to one of the consensus sequences identified by Kabat.

An Fc fragment corresponds to a crystallizable fragment (Fc) or CH2 and CH3 binding domains of Ig, where interaction of Ig with effector molecules or cells occur.

IgG, namely, an abbreviation of Immunoglobulin G, is a main antibody component in a serum, and human IgG has four subtypes of IgG1, IgG2, IgG3 and IgG4 according to r-chain antigenic differences in the IgG molecules.

An incomplete antibody molecule refers to a structure formed by a heavy chain and a light chain of an antibody, in which the heavy chain and the light chain may be linked by a covalent bond or may not be linked by a covalent bond, and is a monoclonal antibody structure that may recognize an antigen.

A Fab fragment is a molecular recognition sequence and an antigen-binding fragment (Fab), which corresponds to two arms of an antibody molecule and consists of a complete variable heavy chain (VH) region and a CH1 region of the light and heavy chains. scFv is a molecular recognition sequence which is a structural isomer of an antibody fragment obtained by genetic engineering of a light chain variable region and a heavy chain variable region of an antibody. The extracellular region of a plasma membrane receptor is a molecular recognition sequence, and the plasma membrane receptor includes an extracellular region generally located on an outer side of a cell and recognizing and binding to the corresponding antigen or ligand; a transmembrane region that may anchor a receptor to a cell surface; and an intracellular region that may have kinase activity or may have a channel that transmits a signal in the cell. A ligand for a plasma membrane receptor refers to a protein, a polypeptide, or a compound that may be recognized and bound by an extracellular region of the plasma membrane receptor. Cytokines are low-molecular-weight soluble proteins produced by various cells induced by immunogens, mitogens, or other stimulators. Cytokines perform various functions, for example, in innate and adaptive immunity, hematopoiesis, cell growth, adult pluripotent stem cells (APSC) regulation, and repairing damaged tissues. Cytokines may be divided into interleukins, interferons, tumor necrosis factor superfamily, colony stimulating factors, chemokines, growth factors, and the like. A protein expression tag refers to an amino acid sequence added at an N-terminal or a C-terminal in a target protein, which may be a small peptide or a long amino acid. The addition of the protein expression tag may facilitate correct folding of a protein, separation and purification of a protein, and reducing degradation of a protein in a cell. Commonly used labels include, but not limited to, HA, SUMO, His, GST, GFP, and Flag.

The type of antibody to be used as a heterodimeric bispecific antibody of the present disclosure is not particularly limited. Preferably, antibodies known in the related art that are useful in treatment and/or prevention of diseases may be used in the present disclosure.

A heterodimeric bispecific antibody of the present disclosure may have at least one substitution, deletion, addition, and/or insertion. For example, some amino acids may replace other amino acids in a structure of a protein without significant loss of ability to bind to other polypeptides (e.g., antigens) or cells. Since the binding capacity and nature of a protein determine biological functional activity of the protein, some amino acid sequences may be substituted in a sequence of the protein without appreciable loss of biological utility or activity.

In many cases, a polypeptide variant may contain at least one conservative substitution. The term "conservative substitution" may refer to substitution of an amino acid with another amino acid having similar properties. One of ordinary skill in the art of peptide chemistry may expect substantially no change may occur in a secondary structure and hydrophilic properties of the polypeptide.

Substitutions of amino acids may be generally based on relative similarity of side chain substituents of the amino acids, such as hydrophobicity, hydrophilicity, charge, size, and the like. The exemplary substitutions with various foregoing characteristics are well known to one of ordinary skill in the art and include: arginine and lysine; glutamate and aspartate; serine and threonine; glutamine and asparagine; and valine, leucine, and isoleucine.

The term "identity" as used in the present disclosure has a meaning known in the art, and one of ordinary skill in the art may also be familiar with the rules and criteria for determining the identity between different sequences, referring to a homology percentage of identical residues between a sequence of a variant of a polynucleotide or polypeptide and a non-variant thereof after sequence alignment and introduction of gaps (if necessary, after obtaining the maximum percent of homology). In the present disclosure, in a case where the definition of identity is satisfied, an obtained variant sequence may have the same biological activity as the parent sequence. Methods and means for screening variant sequences using the activities are well known to one of ordinary skill in the art. Such variant sequences may be readily obtained by one of ordinary skill in the art in light of the teachings of the present disclosure. In an example embodiment, a variant of a polynucleotide or a polypeptide may have a polynucleotide or polypeptide identity of at least about 70%, at least about 75%, at least about 80%, at least about 90%, at least about 95%, at least about 98%, at least about 99%, at least about 99.1%, 99.2%, 99.3%, 99.4%, 99.5%, 99.6%, 99.7%, 99.8%, or 99.9%, as compared with the polynucleotide or the polypeptide, respectively. Due to redundancy of a genetic code, variants of these sequences encoding the same amino acid sequence may be present.

Another embodiment of the present disclosure includes a polynucleotide composition in which a polynucleotide sequence according to the present disclosure, a fragment thereof, or a complementary sequence thereof are hybridized under moderate to highly stringent conditions. Hybridization techniques are well known in the art of molecular biology. For the purpose of illustration, suitable moderately stringent conditions for testing the hybridization of a polynucleotide of the present disclosure to another polynucleotide include: pre-washing in a solution of 5× saline sodium citrate (SSC), 0.5% SDS, and 1.0 millimolar (mM) EDTA (pH 8.0); overnight hybridization at a temperature in a range of 50° C. to 60° C. in 5×SSC; and then washing twice in each SSC containing 0.1% SDS at 2×, 0.5×, and 0.2× for 20 minutes at a temperature of 65° C. One of ordinary skill in the art may understand that stringency of hybridization may be readily manipulated, such as by varying a salt content of a hybridization solution and/or a temperature at which the hybridization occur. For example, in another embodiment, suitable highly stringent hybridization conditions include the conditions described above in addition to an elevated hybridization temperature in a range of, for example, 60° C. to 65° C. or 65° C. to 70° C.

A host cell of the present disclosure may be any cell that may be used in exogenous gene expression. The host cell may include, but not limited to, Escherichia coli (E. Coli), yeast, insect cells, plant cells, and mammalian cells.

Vectors of the present disclosure include vectors that may perform replication in any type of cell or organism, for example, including plasmids, bacteriophages, cosmids, and mini-chromosomes. In some embodiments, a vector including a polynucleotide of the present disclosure may be a vector suitable for propagation or replication of a polynucleotide or a vector suitable for expression of a polypeptide of the present disclosure. Such vectors are known in the art and are commercially available.

A "vector" may include both a shuttle vector and an expression vector. In general, a plasmid construct may also include a replication origin (such as a replication origin of ColE1) and a selectable marker (such as ampicillin or tetracycline resistance) for plasmid replication and selection in bacteria, respectively. An "expression vector" refers to a vector including a regulatory sequence or a regulatory element required for expression of an antibody of the present disclosure and including an antibody fragment in a bacterial or eukaryotic cell.

The vector of the present disclosure may be any vector used in exogenous gene expression, including, but not limited to, a plasmid vector. The plasmid vector may include at least one of a replication origin, a promoter, a target gene, a multiple cloning site, and a selection marker gene. Preferably, the vector of the present disclosure may include, but not limited to, a plasmid vector, such as a X0GC vector, modified from a pcDNA vector.

A subject of the present disclosure includes birds, reptiles, mammals, and the like. Preferably, the mammals include rodents, primates, and preferably, humans.

The disease in the present disclosure includes, but not limited to, tumors, and preferably, the tumors may include diseases such as leukemia, lymphoma, myeloma, brain tumors, head and neck squamous cell carcinoma, non-small cell lung cancer, nasopharyngeal cancer, esophageal cancer, stomach cancer, pancreas cancer, gallbladder cancer, liver cancer, colorectal cancer, breast cancer, ovarian cancer, cervical cancer, endometrial cancer, uterine sarcoma, prostate cancer, bladder cancer, renal cell carcinoma, and melanoma.

A pharmaceutically acceptable carrier refers to a pharmaceutical carrier commonly used in the pharmaceutical field, such as diluents; excipients and water; fillers such as starch; sucrose, lactose, or microcrystalline cellulose; binders such as cellulose derivatives, alginates, gelatin, and polyvinyl pyrrolidone; wetting agents such as glycerin; disintegrating agents such as sodium carboxymethyl starch, hydroxypropyl cellulose, croscarmellose, agar, calcium carbonate, and sodium bicarbonate; absorption enhancers such as quaternary ammonium compounds; surfactants such as cetyl alcohol and sodium lauryl sulfate; adsorption carriers such as aged soil and soap clay; lubricants such as talc, calcium, and magnesium stearate, micronized silica gel, polyethylene glycol, and the like. Adjuvants, such as flavoring agents, sweeteners, and the like may also be added to a composition.

The present disclosure will be further clarified by the following non-limiting examples, which are known to one of ordinary skill in the art, and many modifications may be made thereto without departing from the spirit and scope of the present disclosure.

The following experimental methods are general methods unless otherwise specified, and the experimental materials used may be easily obtained from commercial companies unless otherwise specified. The various antibodies used in the following Examples of the present disclosure are all derived from standard antibodies of the commercial route.

Example 1

Construction of Vector of Anti-PD-1/Anti-HER2 Heterodimeric Antibody Molecule An X0GC expression vector of the heavy chain and the light chain of the anti-human PD-1 was obtained, wherein the nucleotide sequence of the light chain variable region was as shown in the SEQ ID NO: 9, and the amino acid sequence was as shown in the SEQ ID NO:10. The nucleotide sequence of the light chain constant region was as shown in the SEQ ID NO: 3, and the amino acid sequence was as shown in the SEQ ID NO: 4. The nucleotide sequence of the heavy chain variable region was as shown in the SEQ ID NO: 11, and the amino acid sequence was as shown in the SEQ ID NO: 12. The nucleotide sequence of the heavy chain constant region was as shown in the SEQ ID NO: 13, and the amino acid sequence was as shown in the SEQ ID NO: 14. The light chain variable region, the light chain constant region, the heavy chain variable region, and the heavy chain constant region were respectively amplified by using a polymerase chain reaction (PCR) method. In the present disclosure, all PCR reactions were carried out using the Phusion high-fidelity DNA polymerase (F-530L, available from New England Biolabs (NEB)). PCR primers were designed according to the principle of base complementation and the need for restriction sites. The reaction system included 8.9 microliters (μL) of $H_2O$, 4 μL of 5× Phusion high-fidelity DNA polymerase buffer solution, 4 μL of 1 mM dNTP, 1 μL of a forward primer, 1 μL of a reverse primer, 0.1 μL of Phusion high-fidelity DNA polymerase, and 1 μL of template. The PCR products of the variable region and the constant region were electrophoresed on a 1.5% agarose gel, and the corresponding fragments were recovered using a DNA recovery kit (product No. A9282, available from Promega). The recovered variable region fragment and the constant region fragment were used as templates, and a forward primer of the variable region and a reverse primer of the constant region were used to perform a PCR reaction once more. Then, the corresponding fragments were recovered to thereby obtain a full-length fragment of the heavy chain and the light chain. The X0GC vector and the full-length fragment were cleaved by using restriction enzymes EcoRI (product No. R3101L, available from NEB) and HindIII (product No. R3104L, available from NEB), and the restriction enzyme system included: 32 μL of 10× buffer solution, 0.5 μL of each of EcoRI and Hind III, 3 μL of the full-length fragment obtained by gel recovery, and 14.5 μL of $H_2O$. The restriction enzyme system was subjected to a reaction at a temperature of 37° C. for 3 hours. The restriction enzyme products were ligated using a T4 DNA ligase (NEB, product No. M0202V), and the reaction system included 2 μL of 10× ligase buffer solution, 0.5 μL of ligase, 3 μL of the full-length fragment obtained by gel recovery, 3 μL of the X0GC vector obtained by gel recovery, and 11.5 μL of $H_2O$. The reaction was allowed to react at room temperature for 12 hours. The ligation products were transformed into an *E. coli* competent cell DH5α (product No. CB104, available from Tiangen), respectively, to thereby obtain an X0GC expression vector of the heavy chain and the light chain of the antibody for expression of the heavy chain and the light chain of the antibody in eukaryotic cells.

An X0GC expression vector of the heavy chain and the light chain of the anti-human HER2 antibody was obtained. The sequence of the antibody variable region was derived from www.drugbank.ca/drugs/DB00072. The nucleotide sequence of the light chain variable region was as shown in the SEQ ID NO: 1, and the amino acid sequence was as shown in the SEQ ID NO: 2. The nucleotide sequence of the light chain constant region was as shown in the SEQ ID NO: 3, and the amino acid sequence was as shown in the SEQ ID NO: 4. The nucleotide sequence of the heavy chain variable region was as shown in the SEQ ID NO: 5, and the amino acid sequence was as shown in the SEQ ID NO: 6. The nucleotide sequence of the heavy chain constant region was as shown in the SEQ ID NO: 7, and the amino acid sequence was as shown in the SEQ ID NO: 8. According to the foregoing method, an X0GC expression vector of a heavy chain and a light chain of an antibody were obtained for expression of the heavy chain and the light chain of the antibody in eukaryotic cells.

Example 2

Expression of Anti-PD-1/Anti-HER2 Heterodimeric Antibody Molecule

The expression vector of a heavy chain and a light chain of an antibody including anti-human PD-1 were transfected into a 293F cell (FreeStyle™ 293-F Cells, product No. R79007, available from Invitrogen), and the expression vector of a heavy chain and a light chain of an antibody including anti-human HER2 were also transfected into a 293F cell. Cells were inoculated one day prior to transfection. Cells were collected by centrifugation on the day of transfection. The cells were resuspended in a fresh FreeStyle™ 293 expression medium (FreeStyle™ 293 Expression Medium, product No. 12338001, available from Gibco) at a cell density of $200 \times 10^5$ cells/mL. A plasmid was added thereto according to the transfection volume at a final concentration of 36.67 µg/mL, and the mixture was gently and homogeneously mixed. Subsequently, linear polyethyleneimine (PEI, linear, molecular weight of (MW) 25,000, product No. 43896, available from Alfa Aesar) was added thereto at a final concentration of 55 µg/mL, and the mixture was gently and homogeneously mixed. Thereafter, the cells were placed in a cell culture incubator and incubated at a temperature of 37° C. for 1 hour in a shaker at a rate of 120 revolutions per minute (rpm). A 19-fold transfection volume of fresh medium was then added thereto. Subsequently, the cells were incubated at a temperature of 37° C. in a shaker at a rate of 120 rpm. The cell culture supernatant transfected for 5 days to 6 days was collected by centrifugation.

The amount of expression was determined by enzymelinked immunosorbent assay (ELISA). The precipitate was removed by filtration using a 0.2 µm filtration film before applying the result to column purification. This process was performed at a temperature of 4° C.

Example 3

Purification of Expression Product of Anti-PD-1/Anti-HER2 Heterodimeric Antibody Molecule Using an AKTA explorer 100 type protein purification system (available from GE Healthcare), and affinity chromatography column rProtein A Sepharose Fast Flow (16 mm I.D., 10 mL, available from GE Healthcare) was purified at a temperature of 4° C. The column was first equilibrated with mobile phase A (20 mM sodium phosphate buffer solution, 150 mM sodium chloride, pH 7.4). After the baseline was stabilized, samples were loaded to the supernatant of the treated cells at a flow rate of 5 mL/min. After the loading of the samples, equilibration was performed using mobile phase A. The sample were each an anti-PD-1 expression product and an anti-HER2 expression product. Subsequently, a 5-column volume was washed using mobile phase B1 (mobile phase A containing 0.5 M arginine). Then, a 5-column volume was eluted using mobile phase B2 (100 mM citric acid, pH 3.0) to collect a target protein at maximum, i.e., the elution peak. The flow rate of the elution was 5 mL/min. The elution peak chromatogram of the anti-PD-1 expression product is shown in FIG. 1. The elution peak of the anti-HER2 expression product was similar with that of the anti-PD-1 expression product (of which the result is not described herein), and the elution peak was collected (the gray area in FIG. 1), and the pH was adjusted to 5.0 by dropwise addition of 1 M sodium acetate solution.

Example 4

Figure 2:
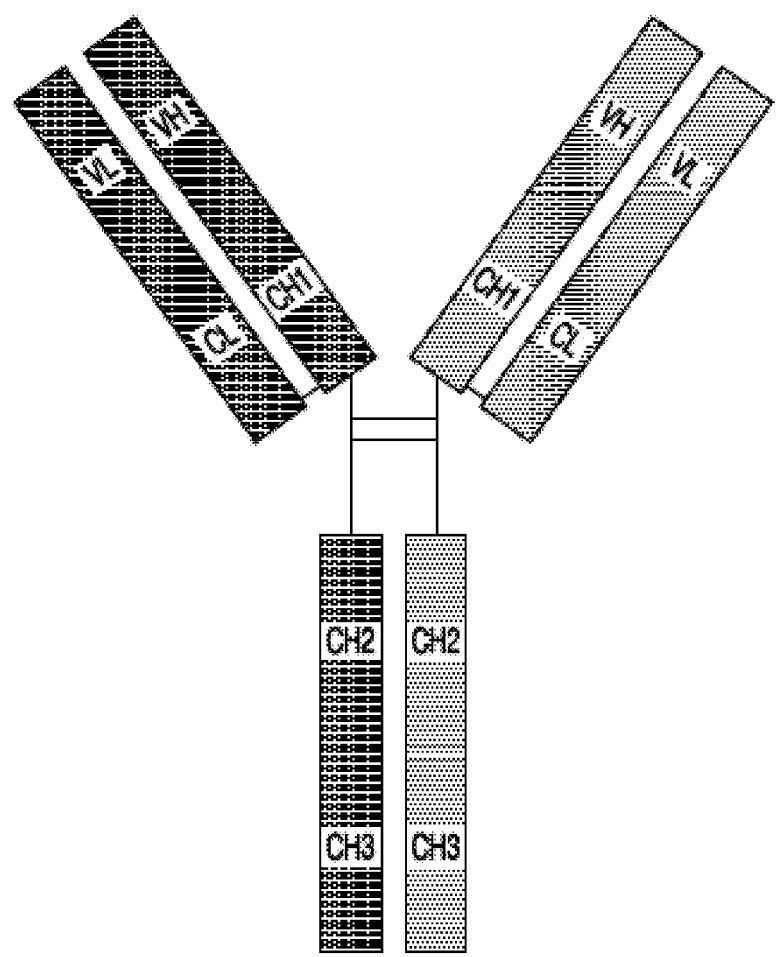
FIG. 2 shows a structure of an anti-PD-1/anti-HER2 heterodimeric antibody molecule.

Preparation and Purification of Anti-PD-1/Anti-HER2 Heterodimeric Antibody Molecule The structure of the anti-PD-1/anti-HER2 heterodimeric antibody molecule is as shown in FIG. 2.

Figure 3:
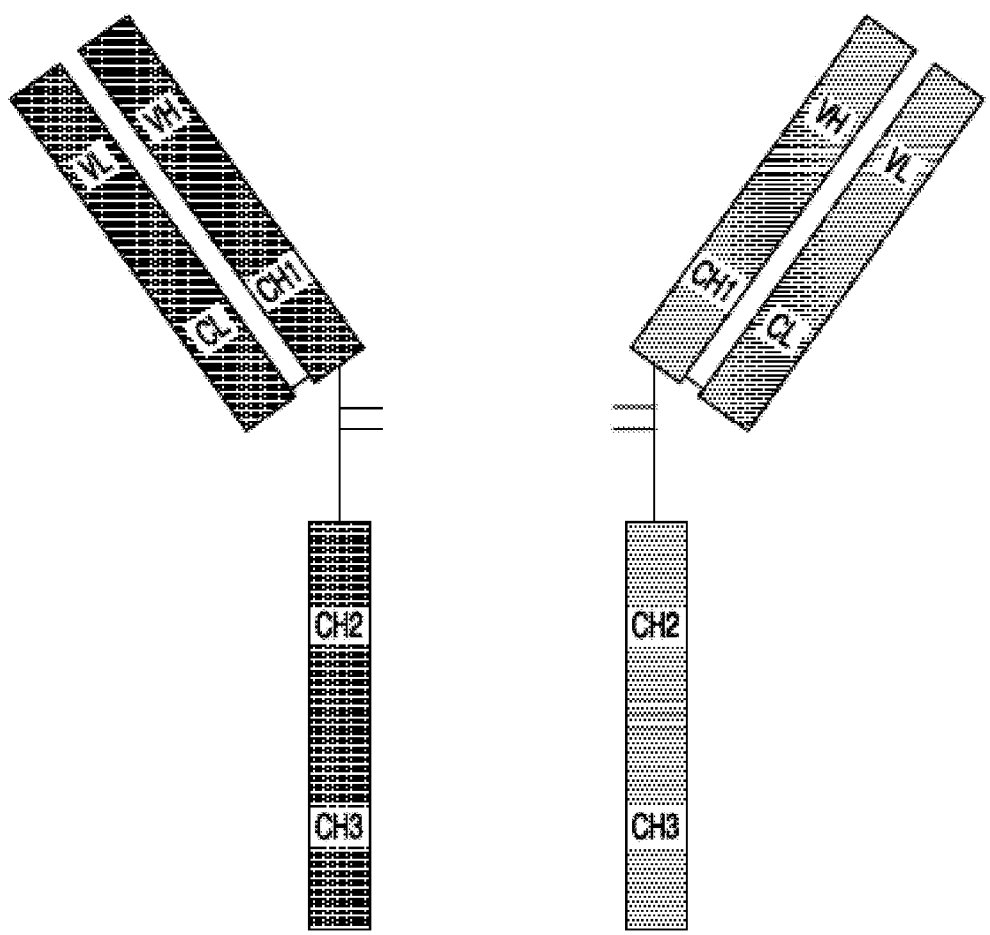
FIG. 3 shows a structure of an incomplete antibody of a heavy chain and a light chain.
Figure 4A:
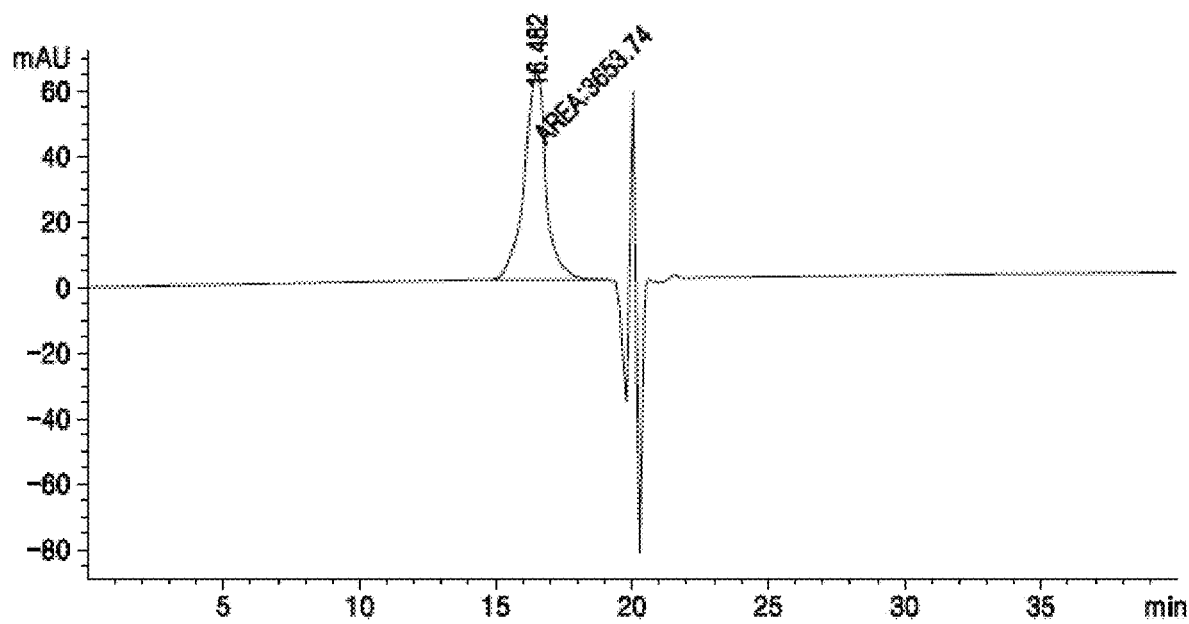
FIG. 4A shows an analysis result of size exclusion chromatography-high-performance liquid chromatography (SEC-HPLC) performed on an anti-PD-1 incomplete antibody of a heavy chain and a light chain.
Figure 4B:
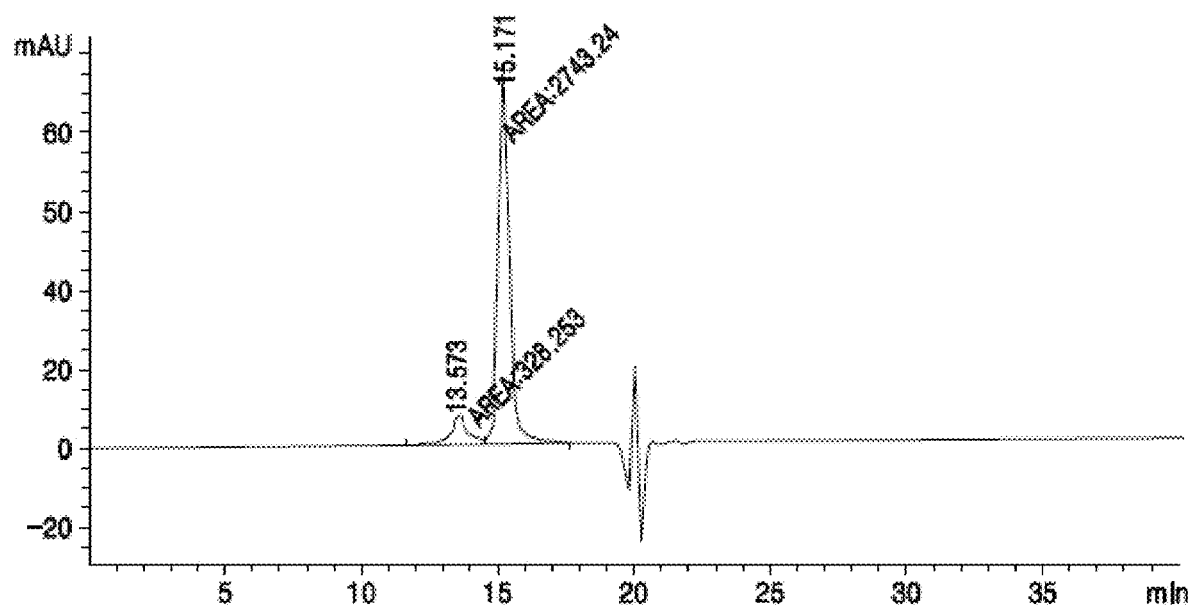
FIG. 4B shows an analysis result of SEC-HPLC performed on an anti-PD-1 incomplete antibody of a heavy chain and a light chain.

The anti-PD-1 expression product and the anti-HER2 expression product obtained by the aforementioned rProtein A Sepharose Fast Flow (16 mm I.D., 10 mL, available from GE Healthcare) were recombined in vitro to obtain a heterodimer. First, the purified and collected protein solution was concentrated by ultrafiltration through an ultrafiltration tube (standard molecular weight cutoff of 10 kiloDaltons (kDa)), and the solution was replaced with the phosphate buffer saline (PBS) solution (pH=7.4). PBS at a concentration of 1 mg/mL and 1M DTT having a final volume of 1/200 were added to the obtained anti-PD-1 and anti-HER2 purified expression product solutions. The final concentration of DTT was 5 mM. Reduction was performed at a temperature of 4° C. (3 to 8 hours), and through the reduction, disulfide bonds were opened, and the disulfide bonds of a hinge region of a small amount of the antibody homodimeric molecules contained in the anti-PD-1 and anti-HER2 expression products were also opened, thus forming an incomplete antibody molecule containing a heavy chain and a light chain. The structure thereof is as shown in FIG. 3. The reduced sample was analyzed by using size exclusion chromatography-high-performance liquid chromatography (SEC-HPLC) (TSKgel superSW3000, available from TOSOH) using 1 mM of a DTT reducing agent in a mobile phase buffer solution. The results thereof are shown in FIGS. 4A and 4B. A ratio of the anti-PD-1 incomplete antibody molecules was 100%, and a ratio of the anti-HER2 incomplete antibody molecules was 89.3%, in which the remaining 10.7% was an aggregate, but no homodimer in which a disulfide bond was opened was present.

Figure 5:
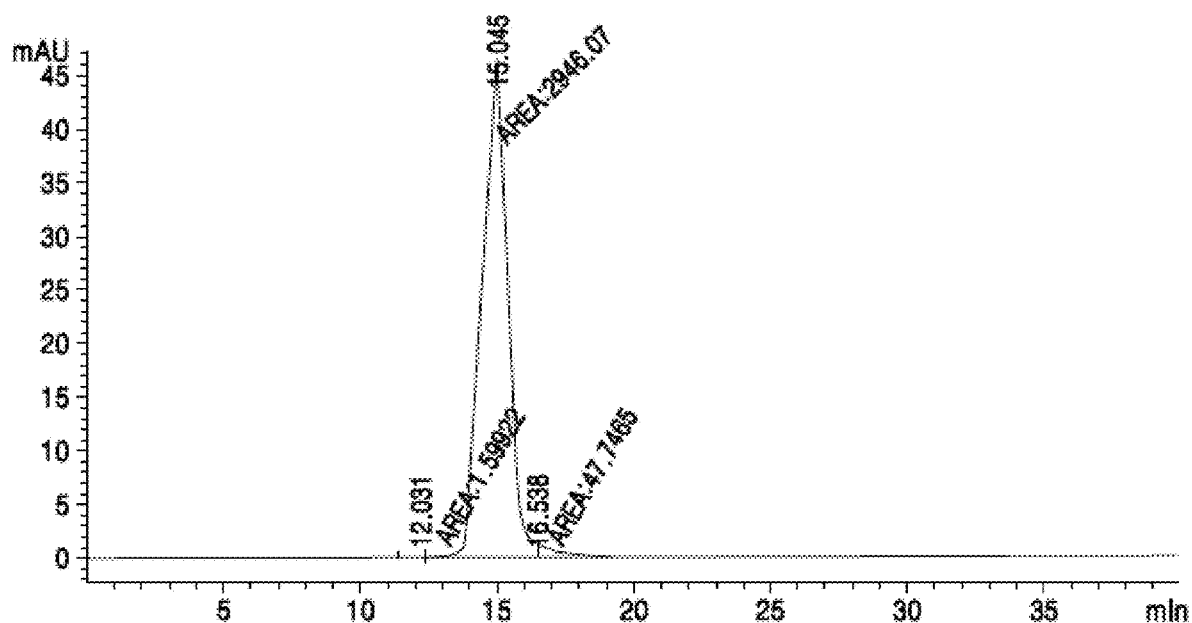
FIG. 5 shows an analysis result of SEC-HPLC performed on an anti-PD-1/anti-HER2 heterodimeric antibody molecule.

The reduced anti-PD-1 and anti-HER2 incomplete antibody molecules were mixed according to a mole ratio under a condition of 4° C. for 24 hours to perform recombination. In the recombination, the anti-PD-1 and anti-HER2 incomplete antibody molecules formed a heterodimeric bispecific antibody including the anti-PD-1 and anti-HER2 incomplete antibody molecules through a non-covalent interaction between CH2 and CH3. Subsequently, the protein solution was subjected to ultrafiltration through an ultrafiltration concentrator (standard molecular weight cutoff of 10 kDa) and replacement with PBS solution (pH=7.4) to complete reduction. Oxidation was then performed by air or by using an oxidizing agent to reform disulfide bonds of the heterodimeric bispecific antibody. The conditions of oxidation included the addition of 100 mM L-dehydroascorbic acid as an oxidizing agent, a final concentration of protein of 1 mg/mL, and a final concentration of the oxidizing agent of 1 mM. Under this condition, oxidation was performed at 4° C. for 24 hours. The sample obtained by the oxidation was subjected to SEC-HPLC analysis, and the results are shown in FIG. 5.

Figure 6:
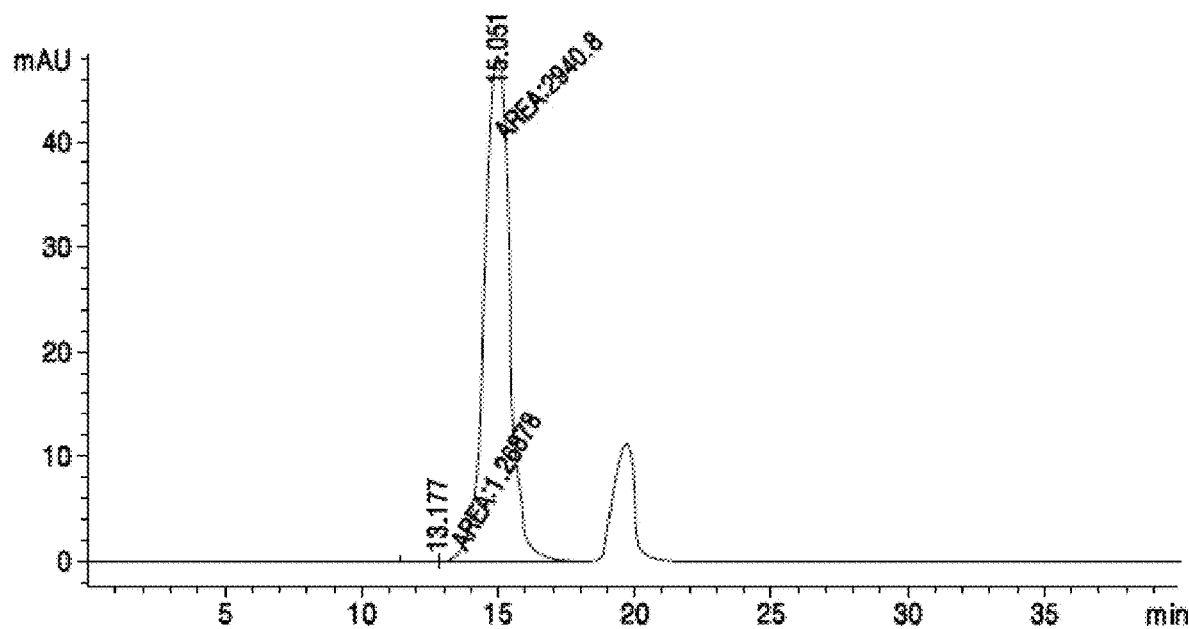
FIG. 6 shows a purity analysis result of SEC-HPLC performed on an anti-PD-1/anti-HER2 heterodimeric antibody molecule.

The heterodimeric antibody molecule obtained by reduction and oxidation of the anti-PD-1 and anti-HER2 incomplete antibody molecules was subjected to ultrafiltration through an ultrafiltration concentrator (standard molecular weight cutoff of 10 kDa) and replacement with 10 mM PBS solution, and the pH was 5.8. Using the AKTA explorer 100 type protein purification system (available from GE Healthcare) and ion chromatography column Source 15S (16 mm I.D., 17 mL, available from GE Healthcare), purification was performed at a temperature of 4° C. The column was first equilibrated with mobile phase A (10 mM sodium phosphate buffer solution, pH 7.0). After the baseline was stabilized, samples were loaded to the treated protein solutions at a flow rate of 3 mL/min. After the loading of the samples, equilibration was performed using mobile phase A. Subsequently, a 20-column volume (0% B to 100% B, 170 min, and at a flow rate of 2 mL/min) was eluted from A (10 mM sodium phosphate, pH 5.8) to B (10 mM sodium phosphate, pH 5.8) to collect the elution peak. The collected protein solution was subjected to ultrafiltration through an ultrafiltration concentrator (standard molecular weight cutoff of 10 kDa), replacement with PBS solution (pH=7.4), and filtration sterilization. The temperature was maintained at 4° C. The purified product was subjected to SEC-HPLC for purity analysis. The results thereof are shown in FIG. 6, and the purity was 99.96%.

Example 5

Stability of Anti-PD-1/Anti-HER2 Heterodimeric Antibody Molecule

Fully sealed 1 mg/mL anti-PD-1/anti-HER2 heterodimer samples were allowed to stand in a climate chamber (KBF240, available from Binder) at a temperature of 40° C. At the corresponding time points (the baseline (the first day), the two weeks, and four weeks), 20 µg of sample was collected to perform SEC-HPLC, thereby performing isolation. The SEC-HPLC conditions were as follows: (1) size exclusion chromatography: TSKgel G3000SWxl (available from Tosoh Bioscience), 5 µm, and 7.8 mm×30 cm; (2) mobile phase: 5 mM PBS, 150 mM NaCl, and pH 6.7; (3) flow rate: 0.6 mL/min; (4) UV detection wavelength: 280 nanometers (nm); and (5) acquisition time: 30 mins. The used instrument was the Agilent 1200 Infinity chromatograph, which was recorded using Agilent ChemStation, and the ratio of the remaining monomers was calculated. As shown in Table. 1, under the experimental conditions of 40° C., the dimers did not undergo significant aggregation. Therefore, the anti-PD-1/anti-HER2 heterodimer is seen as having relatively excellent thermal stability.

TABLE 1

Stability of anti-PD-1/anti-HER2 heterodimeric antibody molecule

| Item | Time | Main peak content (%) | High molecular weight (%) | Low molecular weight (%) | Daily change in main peak content (%) |
|---|---|---|---|---|---|
| Anti-PD-1/ anti-HER2 heterodimeric antibody molecule | Start | 99.42 | 0.32 | 0.26 | 0.09 |
| | Two weeks | 98.69 | 0.25 | 1.06 | |
| | Four weeks | 97.04 | 0.36 | 1.7 | |

Example 6

In Vitro Target Binding Activity of Anti-PD-1/Anti-HER2 Heterodimeric Antibody

The ability of the anti-PD-1/anti-HER2 heterodimeric antibody to bind to a single antigen was determined by using ELISA.

ELISA was performed as follows: recombinant human PD-1 (product No. 10377-H08H, available from Beijing Yiqiao Shenzhou) or human HER2 (product No. 10004-H08H, available from Beijing Yiqiao Shenzhou) was coated on a 96-well high-adsorbing ELISA plate (product No. 42592, available from Costar) with a carbonate buffer solution (0.05 M) at pH 9.6. The coating concentration was 1 µg/mL. The coating amount was 100 µL per well, and the coating was performed at 4° C. overnight. PBST washing was performed five times. The result was sealed at 300 µL/well using PBST containing 1% BSA, and subjected to incubation for 1 hour at 25° C. PBST washing was performed five times. 100 µL of a heterodimeric antibody sample serially diluted in PBST containing 1% BSA, and a control, were added to each well and were incubated for 1 hour at 25° C. PBST washing was performed five times. Subsequently, 100 µL of the horseradish peroxidase-labeled anti-human IgG antibody (product No. AP309P, available from Chemicon) diluted at 1:2,000 in PBST containing 1% BSA was then added to each well, and the cells were incubated for 1 hour at 25° C. PBST washing was performed five times. 100 µL of the colorimetric substrate TMB was added to each well, and color development was allowed to occur for 10 minutes at room temperature. Color development was stopped by adding 100 µL of 1 M $H_2SO_4$ to each well. The absorbance at 450 nm was read on a microplate reader.

Figure 7A:
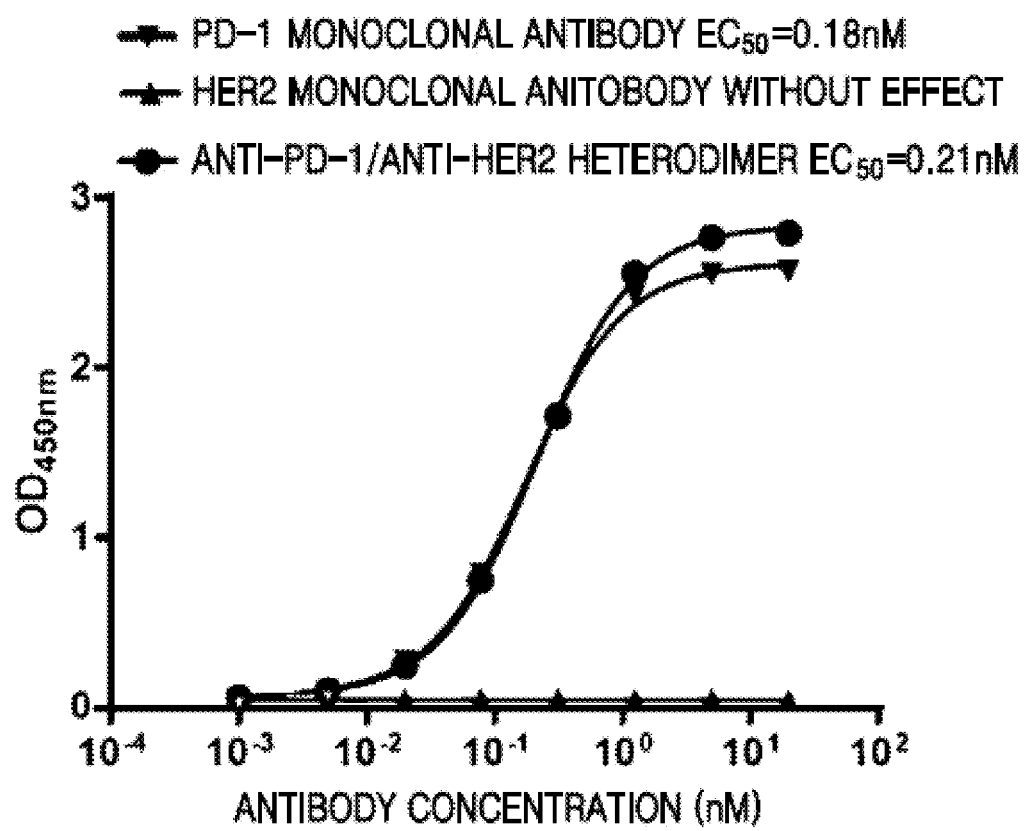
FIG. 7A shows affinity of an anti-PD-1/anti-HER2 heterodimeric antibody for PD-1.
Figure 7B:
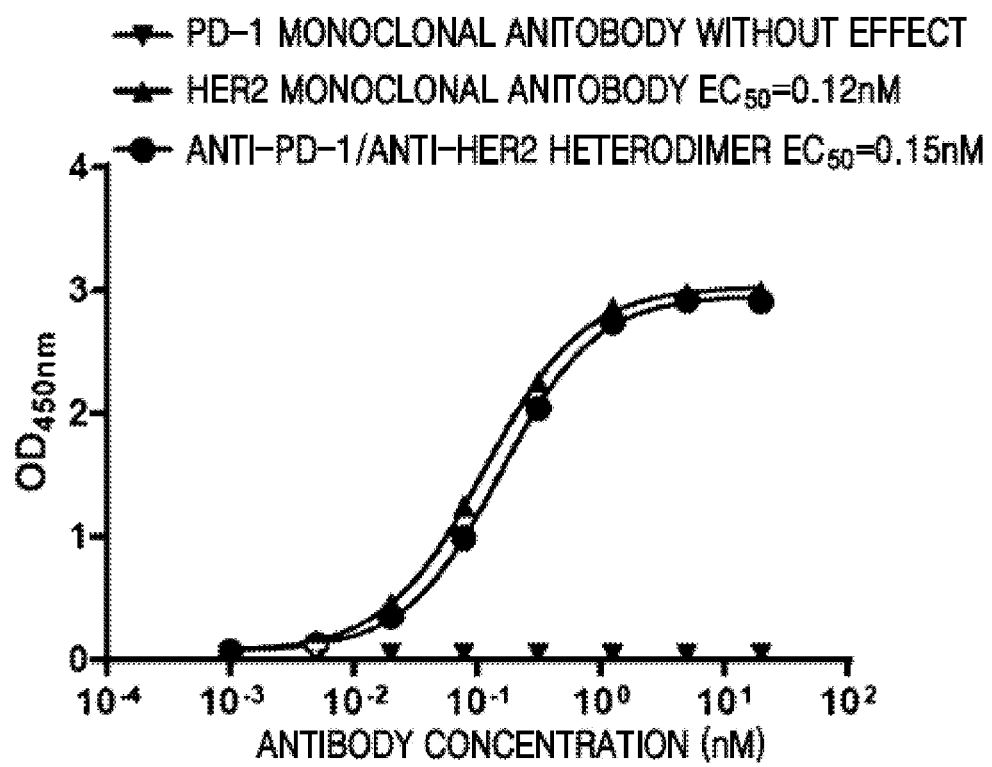
FIG. 7B shows affinity of an anti-PD-1/anti-HER2 heterodimeric antibody for HER2.

As a result, as shown in FIGS. 7A and 7B, it was found that the anti-PD-1/anti-HER2 heterodimeric antibody had high affinity for PD-1 and HER2, thus maintaining antigen-affinitive activity of the bivalent monoclonal antibody.

Example 7

Simultaneous Dual-Targeted Binding Activity of Anti-PD-1/Anti-HER2 Heterodimeric Antibody The simultaneous binding ability of the anti-PD-1/anti-HER2 heterodimeric antibody to two different antigens was measured by using ELISA.

ELISA was performed as follows: recombinant human HER2 (product No. 10004-H08H, available from Beijing Yiqiao Shenzhou) was coated on a 96-well high-adsorbing ELISA plate with a carbonate buffer solution at pH 9.6. The coating concentration was 1 µg/mL. The coating amount was 100 µL per well, and the coating was performed at 4° C. overnight. PBST washing was performed five times. The result was sealed at 300 µL/well using PBST containing 1% BSA, and subjected to incubation for 1 hour at 25° C. PBST washing was performed five times. 100 µL of a heterodimeric antibody sample serially diluted in PBST containing 1% BSA, and a control, were added to each well and were incubated for 1 hour at 25° C. PBST washing was performed five times. Subsequently, 100 µL of biotin-labeled PD-1-Fc (available from Beijing Hanmi Pharmaceutical) diluted in PBST containing 1% BSA was added at 0.5 µg/mL to each well, and the cells were incubated for 1 hour at 25° C. 100 µL of streptavidin-horseradish peroxidase conjugate (product No. 554066, available from BD Pharmingen) diluted at 1:1,000 in PBST containing 1% BSA was then added to each well, and the cells were incubated for 1 hour at 25° C. PBST washing was performed five times. 100 µL of the colorimetric substrate TMB was added to each well, and color development was allowed to occur for 10 minutes at room temperature. Color development was stopped by adding 100 µL of 1 M $H_2SO_4$ to each well. The absorbance at 450 nm was read on a microplate reader.

Figure 8:
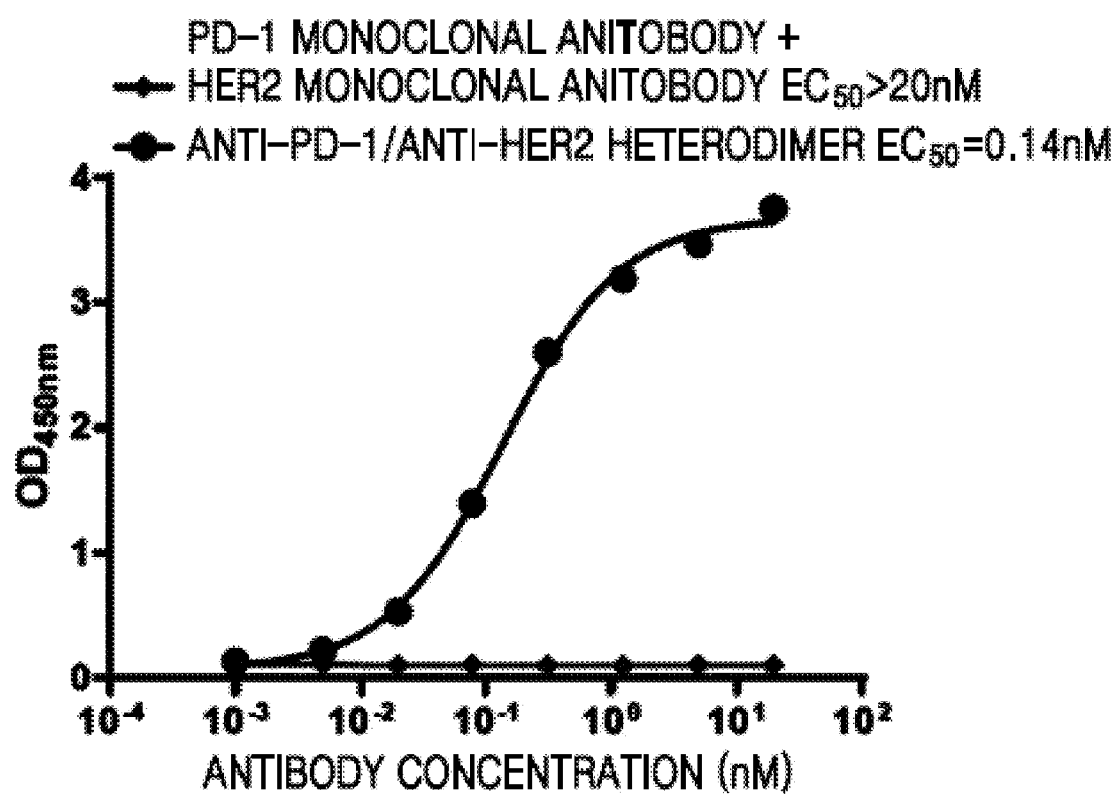
FIG. 8 shows that a combination of a PD-1 monoclonal antibody and a HER2 monoclonal antibody cannot bind to PD-1 and HER2, and an anti-PD-1/anti-HER2 heterodimeric antibody had an activity of binding to two antigens at the same time.

As a result, as shown in FIG. 8, a combination of the PD-1 monoclonal antibody (the sequence of the heavy chain variable region and the sequence of the light chain variable region were identical to the corresponding sequence of the PD-1 binding site in the anti-PD-1/anti-HER2 heterodimeric antibody) and the HER2 monoclonal antibody (Trastuzumab) failed to bind to both PD-1 and HER2 simultaneously, and the anti-PD-1/anti-HER2 heterodimeric antibody only had activity of binding to the two antigens at the same time.

By using a flow cytometer (FCM, FACS Calibur, available from BD Biosicences), simultaneous binding ability of the anti-PD-1/anti-HER2 heterodimeric antibody to dual-targeted antigens was measured using high-PD-1-expressing CHO/PD-1 (product No. M00529, available from GenScript) cells and high-HER2-expressing SK-BR-3 cells.

The CHO/PD-1 cells were stained according to instructions of the PKH26 reagent kit (product No. SLBH4568V, available from Sigma). Briefly, the CHO/PD-1 cells were collected and washed once in a serum-free medium. Then, CHO/PD-1 was prepared as a $2 \times 10^7$/mL cell suspension using Diluent C, the PKH26 reagent kit. Then, PKH26 dye was diluted to 4 µM and mixed with the cell suspension at a ratio of 1:1. A cell density of the mixture suspension was $1 \times 10^7$/mL, and a concentration of PKH26 was 2 µM. The mixture suspension was incubated at room temperature for 1 hour. Subsequently, incubation was performed using an equal volume of fetal bovine serum (FBS) for 1 minute, thereby completing the staining. The result was centrifuged at a centrifugal force of 400 g for 10 minutes, washed twice with complete medium, and resuspended in complete medium for later use. The SK-BR-3 cells were stained according to the instructions of the CFSE reagent kit (product No. C34554, available from Life technology). Briefly, CFSE was diluted with PBS at a working concentration of 0.5 and pre-heated at a temperature of 37° C., and the SK-BR-3 cells were collected by centrifugation at a rate of 1,000 rpm for 5 minutes. The SK-BR-3 cells were resuspended in the pre-heated CFSE working solution and incubated at a temperature of 37° C. for 15 minutes, and then, the cells were collected by centrifugation at a rate of 1,000 rpm for 5 minutes. Next, the cells were resuspended in complete medium and incubated for 30 minutes. Thereafter, the cells were washed using complete medium, and resuspended to thereby completing the preparation. The stained cells were centrifuged and collected, and washed once with cold PBS containing 2% FBS. The cells were resuspended in cold PBS containing 2% FBS such that the cell density was $5 \times 10^6$/mL. The SK-BR-3 cells and the CHO/PD-1 cells were mixed at a ratio of 1:1, and 100 µL of each of the cells were collected from flow pipes, respectively, (that is, $2.5 \times 10^5$ SK-BR-3 cells and $2.5 \times 10^5$ CHO/PD-1 cells). Next, 100 µL of the diluted heterodimeric antibody sample, the control, and the isotype control (human immunoglobulin, available from Jiangxi Boya Bio-Pharmaceutical, State Food and Drug Administration (SFDA) Approval No. S19993012) were added to cold PBS containing 2% FBS at a final concentration of 5 nM. The flow pipe was incubated on ice for 30 minutes. The cells were then washed with PBS containing 2% FBS. The cells were resuspended in 500 µL of cold PBS, and the cells were suspended in a flow cytometer to perform measurement analysis.

Figure 9:
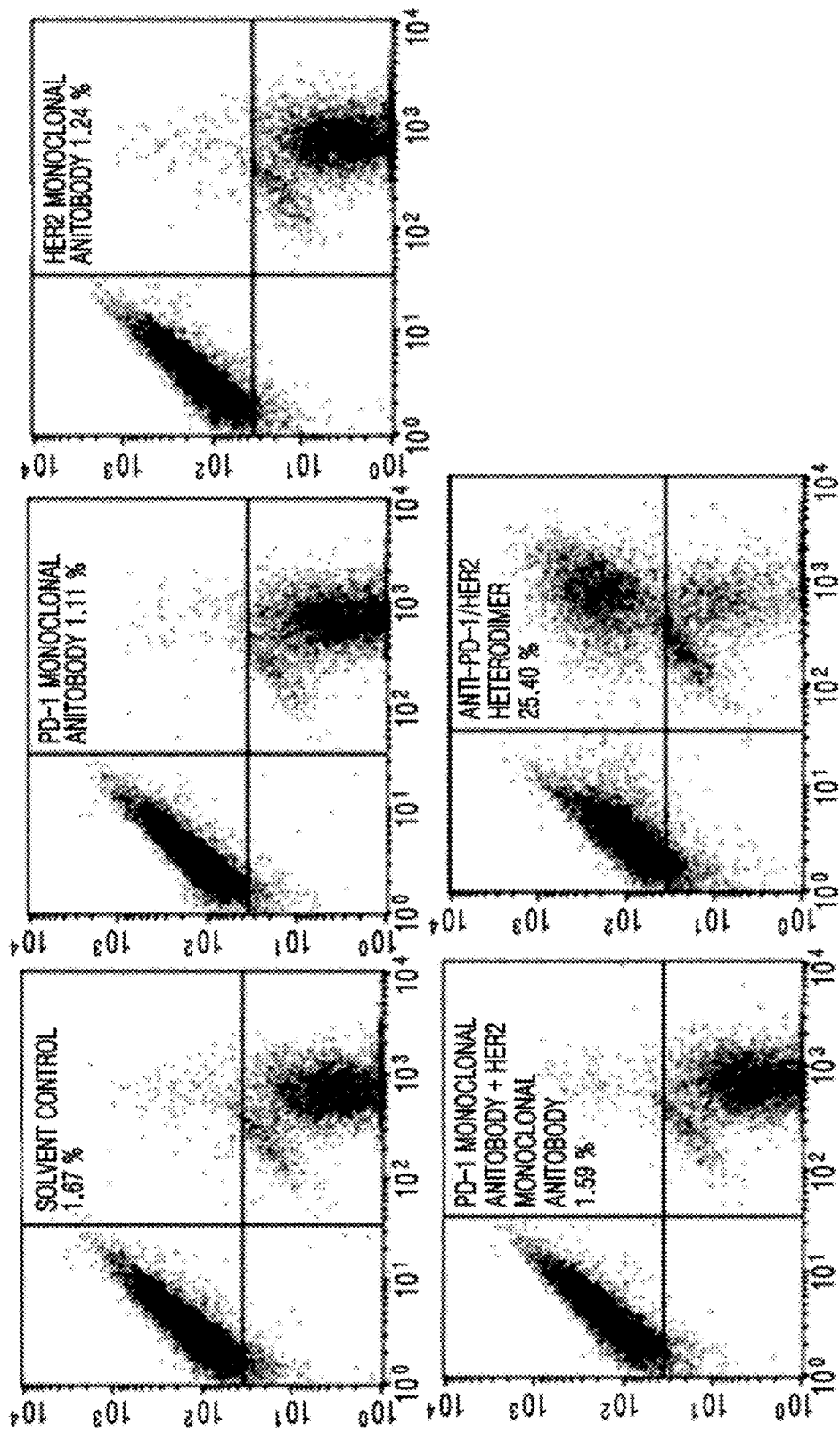
FIG. 9 shows that an anti-PD-1/anti-HER2 heterodimeric antibody induced mutual approach of a SK-BR-3 and CHO/PD-1 cells.

As a result, as shown in FIG. 9, it was found that the heterodimeric antibody simultaneously bound to the high-PD-1-expressing CHO/PD-1 cells and the high-HER2 expressing SK-BR-3 cells. Thus, the anti-PD-1/anti-HER2 heterodimeric antibody were capable of attracting SK-BR-3 cells to CHO/PD-1 cells.

Example 8

Blocking Activity of Anti-PD-1/Anti-HER2 Heterodimeric Antibody on Binding Between PD-1 and Ligand PD-L1 or PD-L2

The blocking activity of the anti-PD-1/anti-HER2 heterodimeric antibody on binding between PD-1 and PD-L1 and binding between PD-1 and PD-L2 was measured by using ELISA.

Recombinant human PD-1-Fc was coated on a 96-well high-adsorbing ELISA plate with PBS at pH 9.6. The coating concentration was 1 µg/mL. The coating amount was 100 µL per well, and the coating was performed at 4° C. overnight. PBST washing was performed five times. The result was sealed at 300 µL/well using PBST containing 1% BSA, and subjected to incubation for 1 hour at 25° C. PBST washing was performed five times. A heterodimer sample and the control serially diluted in PBST containing 1% BSA were added thereto, followed by addition of 100 µL of biotin-labeled PD-L1-Fc at a final concentration of 1 µg/mL or biotin-labeled PD-L2 at a final concentration of 4 µg/mL to each well. Then, the cells were incubated for 1 hour at 25° C. PBST washing was performed five times. Subsequently, 100 µL of the horseradish peroxidase-labeled streptavidin (product No. 554066, available from BD Pharmingen) diluted at 1:1,000 in PBST containing 1% BSA was then added to each well, and the cells were incubated for 1 hour at 25° C. PBST washing was performed five times. 100 µL of the colorimetric substrate TMB was added to each well, and color development was allowed to occur for 10 minutes at room temperature. Color development was stopped by adding 100 µL of 1 M $H_2SO_4$ to each well. The absorbance at 450 nm was read on a microplate reader.

Figure 10B:
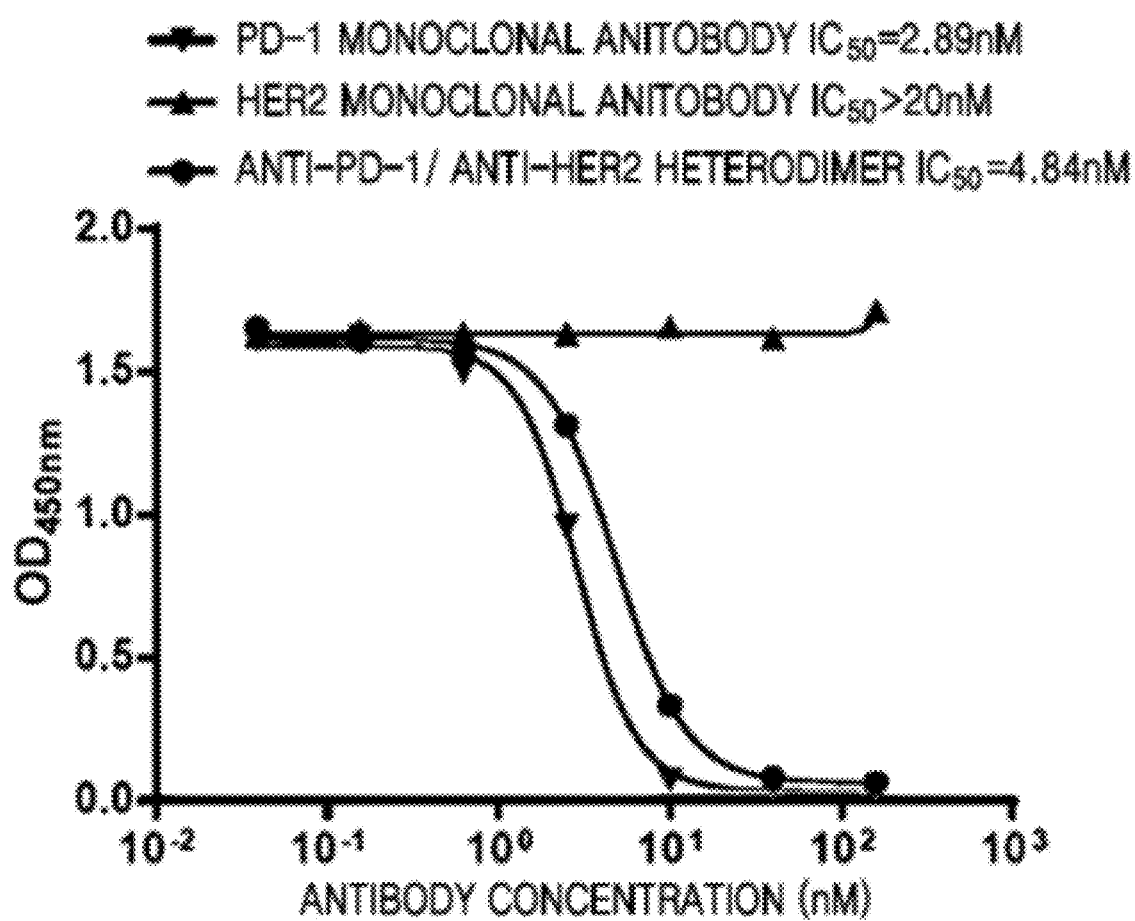

As a result, as shown in FIGS. 10A and 10B, it was found that the anti-PD-1/anti-HER2 heterodimeric antibody blocked binding between PD-1 and PD-L1 and PD-1 and PD-L2, thus maintaining blocking activity of the bivalent monoclonal antibody at a relatively excellent level.

Example 9

T Cell Regulatory Activity of Anti-PD-1/Anti-HER2 Heterodimeric Antibody Molecule The regulatory activity of the anti-PD-1/anti-HER2 heterodimeric antibody on T cell immune reaction was measured by using mixed lymphocyte reaction (MLR).

Acquisition of human dendritic cells (DCs): human peripheral blood mononuclear cells (PBMCs) (product No. CC-2702, available from Lonza) were collected by reproduction. The human PBMCs were resuspended in a serum-free RPMI 1640 medium at a cell density of $5 \times 10^6$/mL and inoculated in a cell culture flask, followed by incubation in a carbon dioxide incubator at 37° C. for 90 minutes. The supernatant and the resuspended cells of the culture solution were discarded, and adherent cells were cultured in complete medium (RPMI 1640 containing 10% FBS). Subsequently, 100 ng/mL GM-CSF (product No. 10016-HNAH, available from Beijing Yiqiao Shenzhou) and 100 ng/mL IL-4 (product No. 11846-HNAE, available from Beijing Yiqiao Shenzhou) were added to the cells. The cells were incubated for three days, followed by a solution change. Then, the cells were incubated again for three days. Next, the medium was changed to complete medium (RPMI 1640 containing 10% FBS) containing 100 ng/mL GM-CSF, 100 ng/mL IL-4, and 20 ng/mL TNF-α, followed by incubation for one day. Accordingly, DCs were obtained.

Acquisition of human T cells: human PBMCs (product No. CC-2702, available from Lonza) were collected by reproduction. The PBMCs and PBMCs from which DCs were generated were each derived from different subjects. Human T cells were isolated according to instructions of the Pan T cell isolation kit (product No. 5150414820, available from Miltenyi Biotech). Briefly, PBMCs were washed with PBS once, and the PBMCs were resuspended in isolation buffer solution (2 mM ethylenediamine tetraacetic acid (EDTA), pH 7.2 PBS containing 0.5% BSA) at a concentration of $10^7$ cells per 40 μL. Then, 10 μL Pan T cell Biotin Antibody Cocktail was added thereto, followed by incubation at a temperature of 4° C. for 5 minutes. Subsequently, 30 μL of isolation buffer solution and 20 μL of Pan T cell MicroBead Cocktail were added thereto, followed by incubation at a temperature of 4° C. for 10 minutes. T cells were then obtained through a magnetic activated cell sorter (MACS) separation column.

The collected human DCs and human T cells were resuspended in complete medium (RPMI 1640 containing 10% FBS) and inoculated on a 96-well plate. The inoculated DCs and T cells were each mixed and cultured at a concentration of $1\times10^4$/well, $1\times10^5$/well, respectively. The heterodimeric antibody sample serially diluted in complete medium and the control were added thereto. The incubation plate was placed in a carbon dioxide incubator at 37° C. and incubated for five days. Once the incubation was complete, the supernatant in the wells was taken to detect cytokine IFN-γ (product. No. ELH-IFNg, available from RayBiotech) according to the kit manual.

Figure 11:
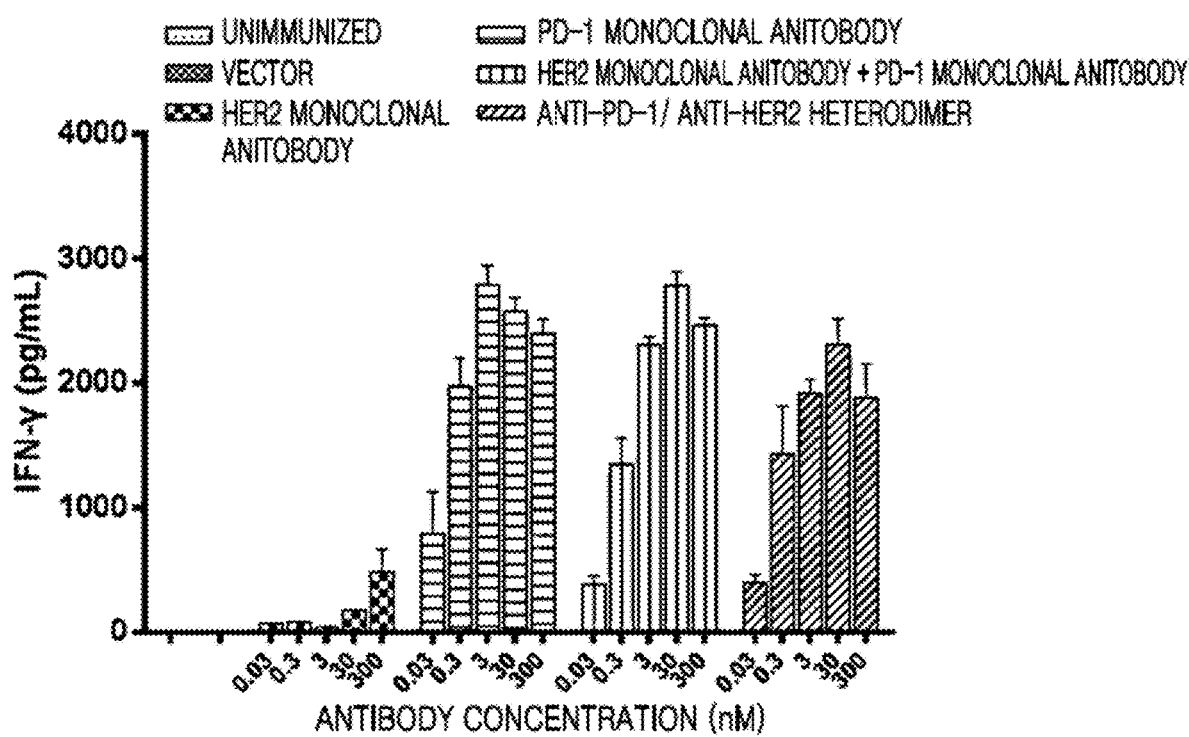
FIG. 11 shows that an anti-PD-1/anti-HER2 heterodimeric antibody exhibited T cell regulatory activity comparable to a PD-1 monoclonal antibody and significantly promoted secretion of cytokine IFN-γ

As shown in FIG. 11, human T cells activate secretion of IFN-γ under the stimulation of allogeneic DCs. When PD-1 monoclonal antibodies are added, activation of T cells may be enhanced, and secretion of cytokines may be promoted. However, HER2 monoclonal antibodies do not have such activity. The anti-PD-1/anti-HER2 heterodimeric antibody exhibited T cell regulatory activity comparable to a PD-1 monoclonal antibody and significantly promoted secretion of cytokine IFN-γ

Example 10

Tumor Cell Inhibitory Activity of Anti-PD-1/Anti-HER2 Heterodimeric Antibody Molecule The anti-PD-1/anti-HER2 heterodimeric antibody was tested for killing activity thereof against human breast cancer cells, i.e., SK-BR-3 cells, in the presence of human PBMCs.

SK-BR-3 cells were incubated in an RPMI 1640 medium containing 10% FBS (i.e., complete medium). The SK-BR-3 cells were collected and resuspended in complete medium. 100 μL of the cells were then inoculated in each well of a 96-well incubation plate at a cell density of $5\times10^4$/mL. That is, 5,000 cells were inoculated in each well. Human PBMCs (product No. CC-2702, available from Lonza) were collected by reproduction. The human PBMCs were resuspended in an RPMI 1640 complete medium at a cell density of $5\times10^5$/mL. 50 μL of the cells were then inoculated in each well of a 96-well incubation plate. That is, 25,000 cells were inoculated in each well. A ratio of effective target cells was 5:1. 50 μμL of each of the heterodimeric antibody sample serially diluted in complete medium and the control were added to each well. The incubation plate was placed in an incubator at 37° C. and 5% carbon dioxide for three days of incubation. Once the incubation was complete, PBMCs in the cell incubation plate were washed and removed using a medium. Then, 100 μL of complete medium and 20 μL of MTS (CellTiter96 Aqueous One Solution, product No. G358B, available from Promega) were added thereto for detection of SK-BR-3 cells. The cell incubation plate was subjected to further incubation in the incubator for 3 to 4 hours. Thereafter, the absorbance at 490 nm was read on a microplate reader.

Figure 12:
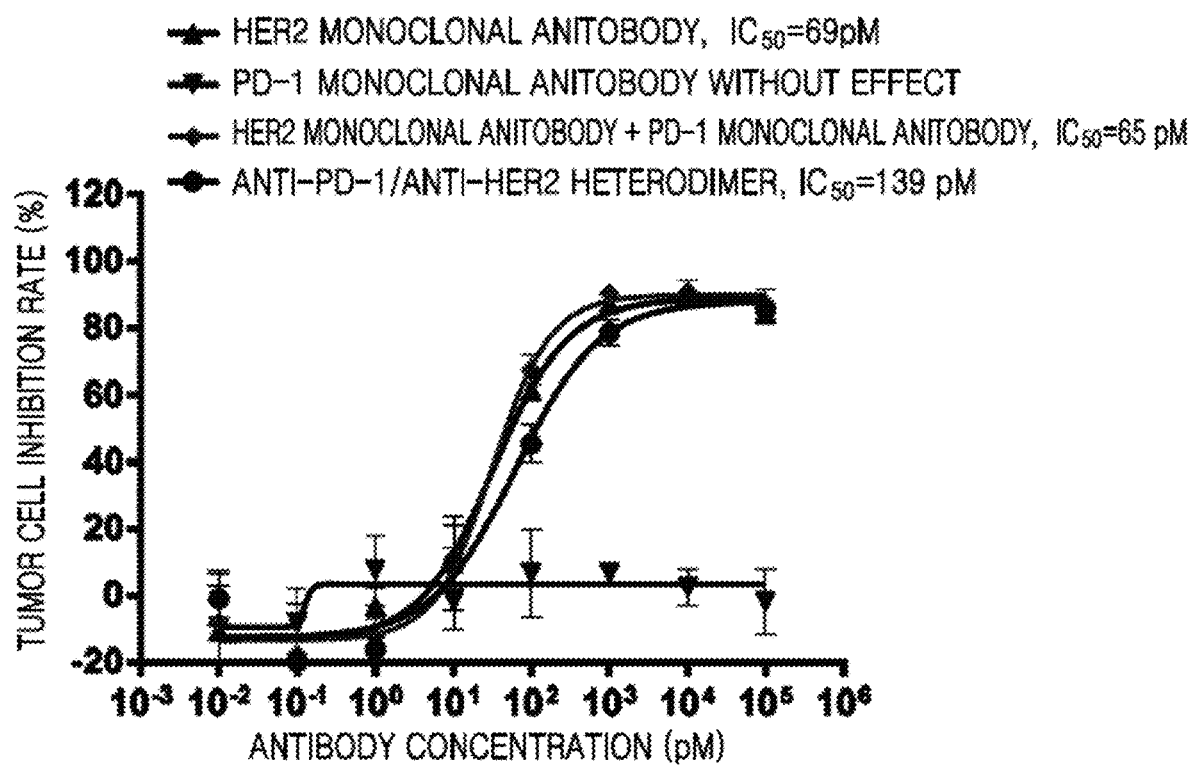
FIG. 12 shows that an anti-PD-1/anti-HER2 heterodimeric antibody monoclonal antibody exhibited tumor cell killing inhibitory activity comparable to HER2.

As shown in FIG. 12, when HER2 monoclonal antibodies were added, the HER2 monoclonal antibodies killed and inhibited SK-BR-3 cells; however, PD-1 monoclonal antibodies did not exhibit such activity in vitro. The anti-PD-1/anti-HER2 heterodimeric antibody also exhibited tumor cell-killing inhibitory activity comparable to the HER2 monoclonal antibodies.

Example 11

Studies in Anti-Tumor Efficacy of Anti-PD-1/Anti-HER2 Heterodimeric Antibody Molecule in Animals The experimental materials were selected from 6- to 8-week-old female immunodeficient NCG mice (available from Nanjing Biomedical Research Institute of Nanjing University). One week after the mice adapted to the environment, $5\times10^6$ human breast cancer cells were subcutaneously inoculated in the right dorsal side of each mouse. Once a length of the tumor volume reached about 100 cubic milimeters (mm3), the mice were grouped according to tumor volume, each group including 8 mice. First, the mice immune system was partially humanized by administration of human PBMCs, and $5\times10^6$ cells were intravenously inoculated in each mouse. Subsequently, each solvent (PBS), 35 nanomoles per kilogram (nmol/kg, 5 mg/kg) of the PD-1 monoclonal antibody, 35 nmol/kg (5 mg/kg) of the HER2 monoclonal antibody, a combination of 35 nmol/kg of the PD-1 monoclonal antibody and 35 nmol/kg of the HER2 monoclonal antibody, and 35 nmol/kg (5 mg/kg) of the anti-PD-1/anti-HER2 heterodimeric antibody were administered two times a week for 2 weeks by sequential administration. The administration was performed by intraperitoneal injection. From the start day of administration, the tumor volume was measured three times a week. The relatively long diameter (a) and the relatively short diameter (b) were measured, and the tumor volume was calculated as follows: tumor volume (mm3)=(a×b2)/2. The tumor volume was observed for 3 weeks, that is, observation of the change in tumor volume continued for one more week after administration was stopped.

Figure 13:
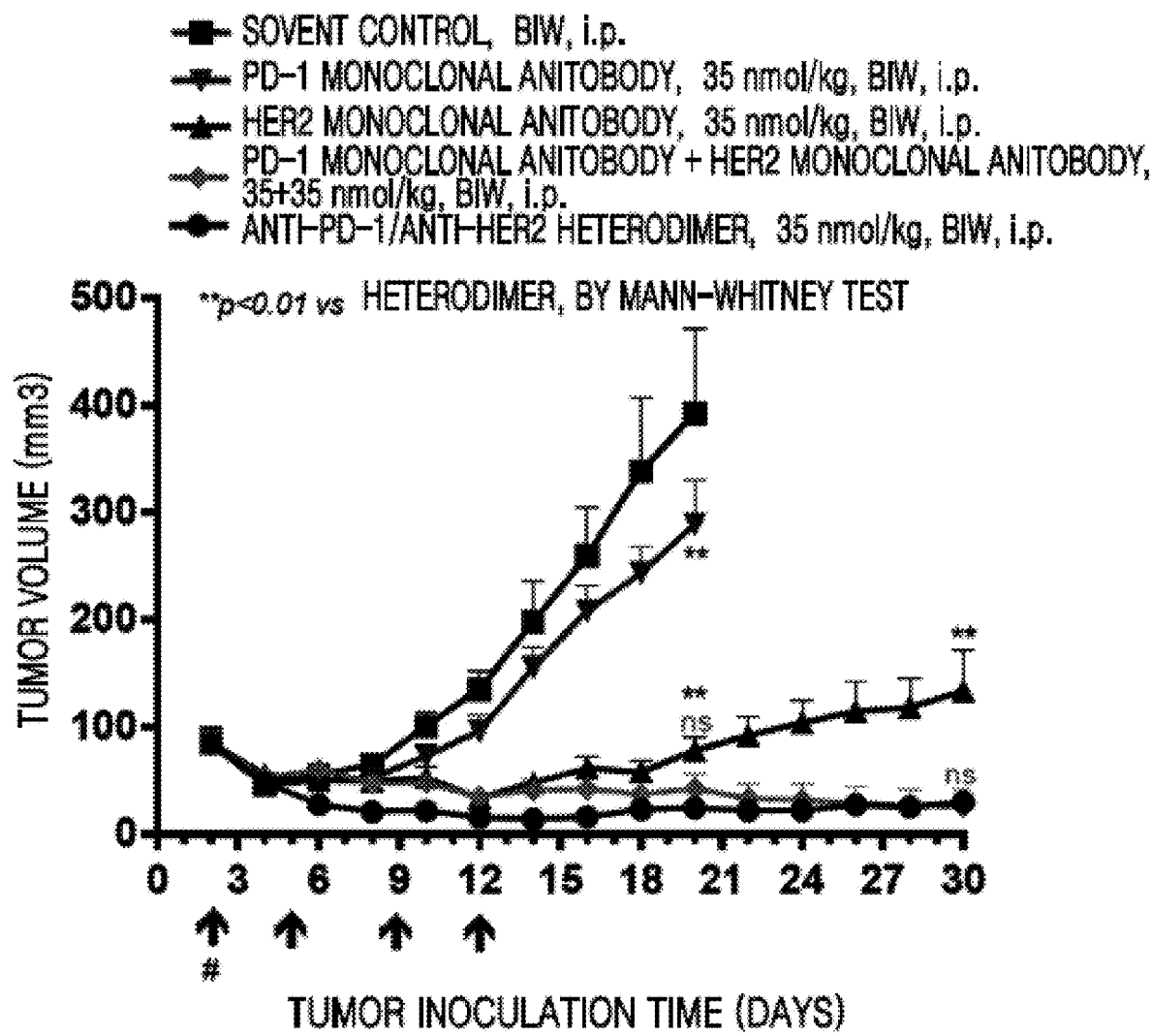
FIG. 13 shows that an anti-PD-1/anti-HER2 heterodimeric antibody exhibited stronger anti-tumor efficacy than a PD-1 monoclonal antibody or a HER2 monoclonal antibody and maintained satisfactory tumor regulatory action after stopping drug administration.

As a result, as shown in FIG. 13, it was found that the anti-PD-1/anti-HER2 heterodimeric antibody had much stronger anti-tumor efficacy than the PD-1 monoclonal antibody and the HER2 monoclonal antibody. Even after administration was stopped, the anti-PD-1/anti-HER2 heterodimeric antibody exhibited moderate tumor inhibitory action.

The invention claimed is:

1. A heterodimeric bispecific antibody comprising:
a first antigen-binding site capable of specifically binding to PD-1 (PD-1 antigen-binding site); and
a second antigen-binding site capable of specifically binding to HER2 (HER2 antigen-binding site),
wherein the bispecific antibody comprises a first Fc chain and a second Fc chain that are linked to each other via at least one disulfide bond,
wherein the first Fc chain and the second Fc chain are each linked to the PD-1 antigen-binding site and the HER2 antigen-binding site, respectively, via a covalent bond or a linking group, or the first Fc chain and the second Fc chain are each linked to the HER2 antigen-binding site and the PD-1 antigen-binding site, respectively, via a covalent bond or a linking group,
wherein an amino acid sequence of an immunoglobulin light chain variable region in the PD-1 antigen-binding site comprises the sequence of SEQ ID NO:10, an amino acid sequence of an immunoglobulin heavy chain variable region in the PD-1 antigen-binding site comprises the sequence of SEQ ID NO: 12,
wherein the first Fc chain and the second Fc chain comprise five amino acid substitutions selected from following (a)-(h):
(a) T366L and D399R substitutions of the first Fc chain and L351E, Y407L, and K409V substitutions of the second Fc chain;
(b) T366L and D399C substitutions of the first Fc chain and L351G, Y407L, and K409C substitutions of the second Fc chain;

(c) T366L and D399C substitutions of the first Fc chain and L351Y, Y407A, and K409P substitutions of the second Fc chain;
(d) T366P and D399N substitutions of the first Fc chain and L351V, Y407P, and K409S substitutions of the second Fc chain;
(e) T366W and D399G substitutions of the first Fc chain and L351D, Y407P, and K409S substitutions of the second Fc chain;
(f) T366P and D399I substitutions of the first Fc chain and L351P, Y407F, and K409F substitutions of the second Fc chain;
(g) T366V and D399T substitutions of the first Fc chain and L351K, Y407T, and K409Q substitutions of the second Fc chain; or
(h) T366L and D399A substitutions of the first Fc chain and L351W, Y407H, and K409R substitutions of the second Fc chain, and
wherein amino acid positions in the above (a)-(h) are numbered according to the Kabat EU Index Numbering System.

2. The heterodimeric bispecific antibody of claim 1, wherein the five amino acid substitutions are (a) T366L and D399R substitutions of the first Fc chain, and L351E, Y407L, and K409V substitutions of the second Fc chain.

3. The heterodimeric bispecific antibody of claim 1, wherein the first and the second Fc chains are derived from immunoglobulin G (IgG).

4. The heterodimeric bispecific antibody of claim 1, wherein the PD-1 antigen-binding site and the HER2 antigen-binding site are each a Fab fragment or an scFv fragment.

5. The heterodimeric bispecific antibody of claim 4, wherein the Fab fragment comprises different first and second heavy chain variable regions and different first and second light chain variable regions.

6. The heterodimeric bispecific antibody of claim 1, wherein the PD-1 antigen-binding site and the HER2 antigen-binding site are each a Fab fragment, or one selected from the PD-1 antigen-binding site and the HER2 antigen-binding site is a Fab fragment, and the other is an scFv fragment.

7. The heterodimeric bispecific antibody of claim 1, wherein, when each of the first Fc chain covalently bonded to the PD-1 antigen binding region and the second Fc chain covalently bonded to the HER2 antigen binding region, or each of the first Fc chain covalently bonded to the HER2 antigen binding region and the second Fc chain covalently bonded to the PD-1 antigen binding region, is present alone in the presence of a reducing agent, the weight ratio of the constituent homodimers are smaller than 50%.

8. The heterodimeric bispecific antibody of claim 1, wherein the HER2 antigen-binding site of the bispecific antibody comprises a light chain variable region comprising the amino acid sequence of SEQ ID NO: 2 and a heavy chain variable region comprising the amino acid sequence of SEQ ID NO: 6.

9. A composition comprising the heterodimeric bispecific antibody of claim 1, and a pharmaceutically acceptable carrier.

* * * * *